United States Patent
Waataja et al.

(10) Patent No.: US 12,311,174 B2
(45) Date of Patent: May 27, 2025

(54) SIMULTANEOUS MULTI-SITE VAGUS NERVE NEUROMODULATION FOR IMPROVED GLYCEMIC CONTROL SYSTEM AND METHODS

(71) Applicant: RESHAPE LIFESCIENCES, INC., Roseville, MN (US)

(72) Inventors: Jonathan James Waataja, Plymouth, MN (US); Raj Nihalani, Irvine, CA (US)

(73) Assignee: RESHAPE LIFESCIENCES INC., Roseville, MN (US)

( * ) Notice: Subject to any disclaimer, the term of this patent is extended or adjusted under 35 U.S.C. 154(b) by 0 days.

(21) Appl. No.: 17/046,677

(22) PCT Filed: Apr. 12, 2019

(86) PCT No.: PCT/US2019/027297
§ 371 (c)(1),
(2) Date: Oct. 9, 2020

(87) PCT Pub. No.: WO2019/200301
PCT Pub. Date: Oct. 17, 2019

(65) Prior Publication Data
US 2021/0146136 A1    May 20, 2021

Related U.S. Application Data

(60) Provisional application No. 62/656,787, filed on Apr. 12, 2018.

(51) Int. Cl.
*A61N 1/00*     (2006.01)
*A61N 1/05*     (2006.01)
(Continued)

(52) U.S. Cl.
CPC ....... *A61N 1/36053* (2013.01); *A61N 1/0509* (2013.01); *A61N 1/0551* (2013.01);
(Continued)

(58) Field of Classification Search
None
See application file for complete search history.

(56) References Cited

U.S. PATENT DOCUMENTS 5,231,988 A    8/1993    Wernicke et al.
6,832,114 B1   12/2004   Whitehurst et al.
(Continued)

FOREIGN PATENT DOCUMENTS

WO    2006/023498 A1    3/2006
WO    2009/124233 A1    10/2009

OTHER PUBLICATIONS

M. Solomonow et al., "Control of Muscle Contractile Force Through Indirect High-Frequency Stimulation", American Journal of Phusical Medicine, 62(2): 71-82.
(Continued)

*Primary Examiner* — John R Downey
*Assistant Examiner* — Anant A Gupta
(74) *Attorney, Agent, or Firm* — Brown Rudnick LLP; Ryan C. Smith

(57) ABSTRACT

Various methods and apparatus for treating a condition associated with impaired glucose regulation in a subject comprising in one embodiment, applying a neural conduction block to a target nerve at a blocking site with the neural conduction block selected to at least partially block nerve pulses. In another embodiment, combinations of down-regulating and or up-regulating with are used to treat impaired glucose regulation. In other embodiments, up-regulation or down-regulation of various nerves, such as the vagus and its branches, are used to modify the secretion of
(Continued)

insulin and glucagon from the pancreas, thereby controlling glucose levels. In yet further embodiments, combinations of down-regulating and or up-regulating are used to control sensitivity of the liver to plasma insulin and glucagon to treat impaired glucose regulation.

20 Claims, 15 Drawing Sheets

(51) Int. Cl.
    *A61N 1/36*     (2006.01)
    *A61N 1/372*     (2006.01)
(52) U.S. Cl.
    CPC ....... *A61N 1/3606* (2013.01); *A61N 1/36171* (2013.01); *A61N 1/37223* (2013.01); *A61N 1/37235* (2013.01)

(56) References Cited

U.S. PATENT DOCUMENTS

| | | | |
|---|---|---|---|
| 7,167,750 | B2 | 1/2007 | Knudson et al. |
| 7,167,751 | B1 | 1/2007 | Whitehurst et al. |
| 8,483,830 | B2 | 7/2013 | Tweden et al. |
| 9,974,955 | B2 * | 5/2018 | Thornton ............ A61N 1/36007 |
| 2004/0172085 | A1 | 9/2004 | Knudson et al. |
| 2004/0172086 | A1 | 9/2004 | Knudson et al. |
| 2004/0172088 | A1 | 9/2004 | Knudson et al. |
| 2004/0176812 | A1 | 9/2004 | Knudson et al. |
| 2005/0038484 | A1 | 2/2005 | Knudson et al. |
| 2005/0131485 | A1 | 6/2005 | Knudson et al. |
| 2006/0190053 | A1 | 8/2006 | Dobak, III |
| 2007/0027484 | A1 | 2/2007 | Guzman et al. |
| 2011/0098762 | A1 | 4/2011 | Rezai |
| 2011/0307023 | A1 * | 12/2011 | Tweden ............. A61N 1/36171 607/40 |
| 2013/0110194 | A1 * | 5/2013 | Wei .................... A61N 1/36171 607/46 |
| 2014/0214129 | A1 | 7/2014 | Waataja et al. |
| 2017/0021174 | A1 * | 1/2017 | Thornton ........... A61N 1/36007 |
| 2019/0125227 | A1 * | 5/2019 | Koya .................. A61N 1/3606 |

OTHER PUBLICATIONS

M. Gershon, "The Second Brain", Harper Collins Publishers: 19 (1999).
K. Uno et al., "Neuronal Pathway from the Liver Modulates Energy Expenditure and Systemic Insulin Sensitivity", Science, 312: 1656-1659 (2006).
B. Peitl et al., "The prandial insulin sensitivity-modifying effect of vagal stimulation in rats", Metabolism Clinical and Experimental 54: 579-583 (2005).
S.E. Kahn et al., "Glycemic Durability of Rosiglitazone, Metformin, or Gluburide Monotherapy", The New England Journal of Medicine, 355;23: 2427-2443 (2006), with correction (N Engl J Med 2007;356:1387).
"Economic Costs of Diabetes in the U.S. in 2007", American Diabetes Association, Diabetes Care 31(3): 1-18 (2008).
M. Matsushita et al., "Important Role of the Hepatic Vagus Nerve in Glucose Uptake and Production by the Liver", Metabolism 49(1): 11-16 (2000).
C. Bernal-Mizrachi et al., "An Afferent Vagal Nerve Pathway Links Hepatic PPARα Activation to Glucocorticoid-Induced Insulin Resistance and Hyoertension", Cell Metabolism 5: 91-102 (2007).
International Search Report and Written Opinion for PCT/US2019/027297 (Aug. 2, 2019).
Search Report for European Patent Application No. 19784437.6 (Jan. 10, 2022).

* cited by examiner

SIMULTANEOUS MULTI-SITE VAGUS NERVE NEUROMODULATION FOR IMPROVED GLYCEMIC CONTROL SYSTEM AND METHODS

CROSS REFERENCE TO RELATED APPLICATION

This application is being filed on 12 Apr. 2019, as a PCT International patent application, and claims the benefit of U.S. Application Ser. No. 62/656,787, filed Apr. 12, 2018, the disclosure of which is incorporated in its entirety.

BACKGROUND

An estimated 29 million people in the United States have diabetes, a serious, lifelong condition. The major forms of diabetes are Type 1 and Type 2. Type 1 diabetes is an autoimmune disease resulting in the destruction of the beta cells in the pancreas so that the pancreas then produces little or no insulin. A person who has Type 1 diabetes must take insulin daily to live. The most common form of diabetes is Type 2 diabetes. In the United States, about 10% of people aged 40 to 59 and 20% of the people 60 years of age and older have Type 2 diabetes. This disease is the sixth leading cause of death and contributes to development of heart disease, stroke, hypertension, kidney disease and nerve damage. Although several treatments are available for diabetes, about 15-32% of the patients fail to maintain glycemic control with monotherapy. (Kahn et al, NEJM 355:23 (2006)) Type 2 diabetes remains a significant health problem and has a cost to the health care system of at least 174 billion dollars. (Dall et al, Diabetes Care 31:1-20 (2008))

Type 2 diabetes is associated with older age, obesity, family history of diabetes, previous history of gestational diabetes, physical inactivity, and ethnicity. When Type 2 diabetes is diagnosed, the pancreas is usually producing enough insulin, but for unknown reasons, the body cannot use the insulin effectively, a condition called insulin resistance. After several years, insulin production decreases, and insulin must be administered orally or via injection to maintain glucose homeostasis, as in Type 1 diabetes.

In the early stages of Type 2 Diabetes, therapy consists of diet, exercise and weight loss, later to be followed by various drugs, which can increase the output of the pancreas or decrease the requirement for insulin, and finally administration of insulin directly. Pharmaceuticals for treatment of diabetes are members of five classes of drugs: sulfonylureas, meglitinides, biguanides, thiazolidinediones, and alpha-glucosidase inhibitors. These five classes of drugs work in different ways to lower blood glucose levels. Some increase insulin output from the pancreas, some decrease glucose output by affecting liver function. Even with such treatment, some patients do not achieve glycemic control.

New therapies for Type 2 Diabetics involving gastric procedures have emerged in the last 10 years, and are increasing in popularity for certain patients. These therapies include various types of gastric bypass, and gastric restrictive techniques. Unexpectedly, these procedures have demonstrated resolution of Type 2 diabetics (for 75-85% of the patients), often within 2-3 days of the procedure, and independent of weight loss. Most patients have been morbidly obese (Body Mass Index, BMI>40), but evolving techniques are allowing the procedures to be applied to patients with BMI>35, and even over-weight or slightly obese patients. However, these surgical options are costly and have risks for the patient both before and after the surgery.

Methods of treating diabetes by upregulating neural activity have been described. Some of these methods for treating diabetes involve directly stimulating pancreatic cells, or parasympathetic/sympathetic tissue which directly innervates the pancreas. For example, U.S. Pat. No. 5,231,988 to Wernicke discloses application of a low frequency electrical signal to the vagus nerve to increase the secretion of endogenous insulin. U.S. Pat. No. 6,832,114 to Whitehurst describes the delivery of low frequency signals to at least one parasympathetic tissue innervating the pancreas to stimulate of pancreatic beta cells to increase insulin secretion. U.S. Pat. No. 7,167,751 to Whitehurst describes methods to relieve endocrine disorders by stimulating the vagus nerve.

Other studies indicate that the role of the vagus nerve with regard to regulation of insulin and blood glucose is not clear. A recent study suggests that damaging the afferent hepatic vagus nerve can inhibit the development of insulin resistance in mice treated with dexamethasone. (Bernal-Mizrachi et al., Cell Metabolism, 2007, 5:91). Some studies indicate that vagotomy induces insulin resistance and in other studies, electrical stimulation induces insulin resistance. (Matsuhisa et al, Metabolism 49:11-16 (2000); Peitl et al., Metabolism 54:579 (2005)). In another mouse model, hepatic vagotomy suppressed increases in insulin sensitivity due to peroxisome proliferator-activated receptor expression. (Uno et al, 2006, Science 312:1656)

Despite the availability of many therapies, Type 2 diabetes remains a major health issue. Many of the therapies have undesirable side effects, do not achieve adequate glycemic control, or adequate glycemic control is not maintained leading to complications from hyperglycemia and also hypoglycemia (low blood glucose typically below 70 mg/dL). Use of pharmaceuticals and/or insulin with the intention to treat hyperglycemia may have the undesired effect of decreasing blood glucose to a level that causes pathophysiological conditions. A temporary decrease in blood glucose can cause, but not limited to, loss of consciousness, stroke, coma, changes in mood or death. Repeated hypoglycemic episodes have been linked to cardiovascular disease. Treatments typically involve consumption of foods high in simple sugars. However, this treatment is not ideal. For example, the onset of hypoglycemia is quick, on the order of minutes, and a loss of cognitive ability may render the subject unable to obtain and consume foods with simple sugars. Thus, there remains a need to develop systems and methods for regulating glucose and/or treating diabetes.

SUMMARY

This disclosure describes methods and systems for treating impaired glucose regulation in a subject. A system comprises a programmable pulse generator (neuroregulator) with a lead and at least one electrode, the electrodes being placed on, or in close proximity to, target nerves or organs. In some embodiments, the system comprises at least two leads and the therapy is delivered across each electrode on the leads.

This disclosure is directed to methods and systems for treating a condition associated with impaired plasma glucose regulation such as Type 2 diabetes, impaired glucose tolerance, and/or impaired fasting glucose. Patients having impaired glucose tolerance and/or impaired fasting glucose are also referred to as having prediabetes. In an embodiment, a method comprises treating a condition associated with impaired plasma glucose regulation in a subject comprising: applying an intermittent (or continuous) neural signal to a target nerve at a site with said neural conduction signal selected to down-regulate or up-regulate afferent and/or efferent neural activity on the nerve and with neural activity restoring upon discontinuance of said signal. In some embodiments, patients are selected that have Type 2 diabetes. In other embodiments, subjects are patients having impaired glucose tolerance and/or impaired fasting glucose.

In embodiments, a method provides for treating a condition associated with impaired glucose regulation in a subject comprising: applying an intermittent (or continuous) electrical signal to a target nerve of the subject having impaired blood plasma glucose regulation, with said electrical signal selected to down-regulate neural activity on the nerve and to restore neural activity on the nerve upon discontinuance of said signal. In embodiments, the electrical signal treatment is selected for frequency, and for on and off times. In some embodiments, the method further comprises applying an electrical signal treatment intermittent (or continuously) multiple times in a day and over multiple days to a second target nerve or organ, wherein the electrical signal has a frequency selected to upregulate and/or down-regulate activity on the target nerve and has an on time and an off time, wherein the off time is selected to allow at least a partial recovery of the activity of the target nerve. In some embodiments, the method further comprises administering a composition to the subject comprising an effective amount of an agent that improves glycemic control.

In yet other embodiments, methods are directed to modify the amount of plasma insulin, blood glucose, or both. In embodiments, a method of modifying the amount of plasma insulin, blood glucose or both comprises: applying an first intermittent (or continuous) electrical signal to a target nerve, with said first electrical signal selected to down-regulate neural activity on the nerve and to restore neural activity on the nerve upon discontinuance of said signal, wherein the electrical signal is selected to modify the amount of plasma insulin, blood glucose or both. In some embodiments, the method further comprises applying a second electrical signal treatment intermittently (or continuously) to a second target nerve or organ, wherein the second electrical signal has a frequency selected to upregulate activity on the target nerve or organ and to restore neural activity of the second target nerve or to restore activity of the target organ to baseline levels. In another aspect of the disclosure, a system for treating a patient with impaired glucose regulation is provided. In some embodiments, the system comprises: at least two electrodes operably connected to an implantable pulse generator, wherein one of the electrodes is adapted to be placed on a target nerve; an implantable pulse generator that comprises a power module and a programmable therapy delivery module, wherein the programmable therapy delivery module is configured to deliver at least one therapy program comprising an electrical signal treatment applied intermittently (or continuously) multiple times in a day and over multiple days to the target nerve, wherein the electrical signal has a frequency selected to downregulate activity on the target nerve and has an on time and an off time, wherein the off time is selected to allow at least a partial recovery of the activity of the target nerve; and an external component comprising a communication system and a programmable storage and communication module, wherein programmable storage and communication module is configured to store the at least one therapy program and to communicate the at least one therapy program to the implantable pulse generator. In some embodiments, the programmable therapy delivery module is configured to deliver a second therapy program comprising an electrical signal treatment applied intermittently multiple times in a day and over multiple days to a second target nerve or organ, wherein the electrical signal has a frequency selected to upregulate or down-regulate activity on the target nerve and has an on time and an off time, wherein the off time is selected to allow at least a partial recovery of the activity of the target nerve or organ. In other related embodiments, the communication module is configured to store the at least one therapy program and to communicate the at least one therapy program to the implantable pulse generator using a communication system selected from a group consisting of an antenna, blue tooth technology, radio frequency, WIFI, light, sound and combinations thereof such as blue tooth technology, radio frequency, WIFI, light or sound.

DETAILED DESCRIPTION

Figure 1:
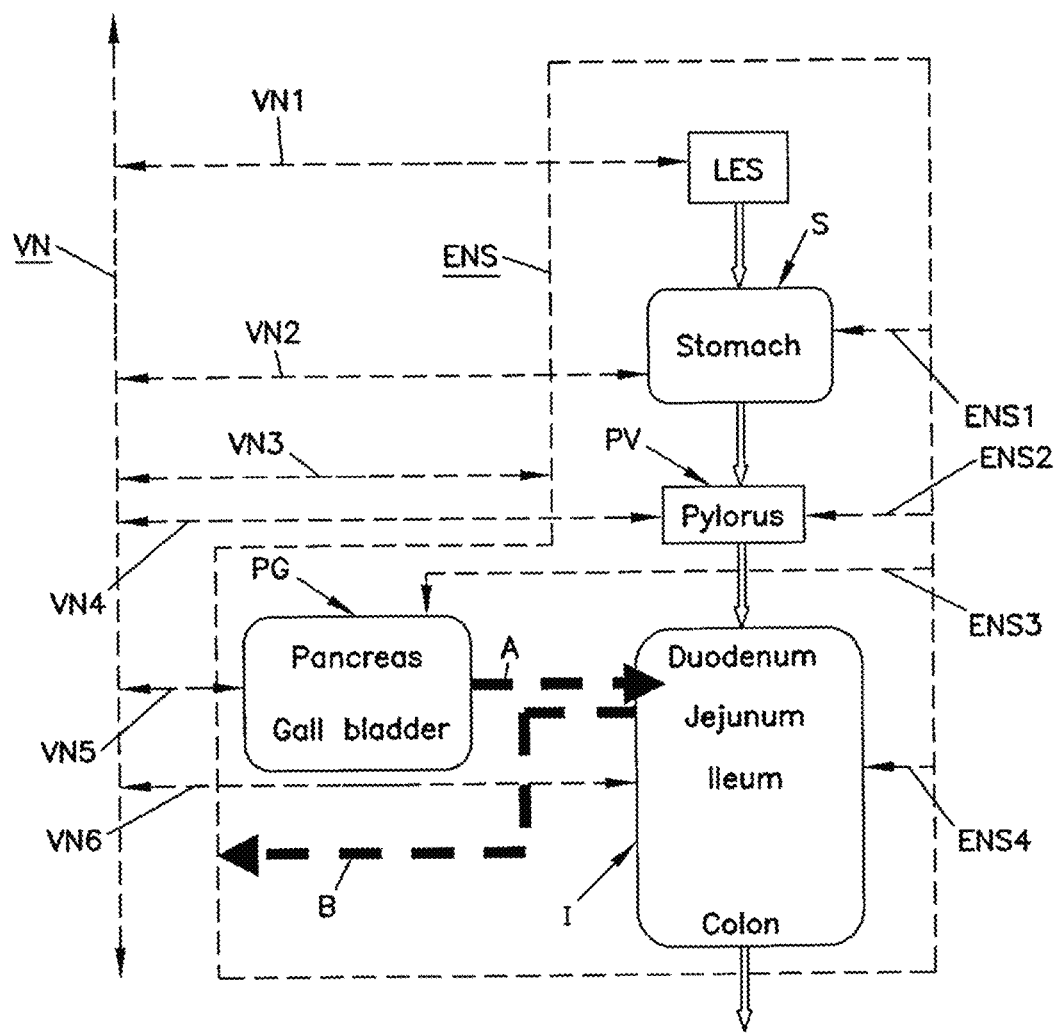
FIG. 1 is a schematic illustration of an alimentary tract (GI tract plus non-GI organs such as the pancreas and liver) and its relation to vagal and enteric enervation.

The following commonly assigned patent and U.S. patent applications are incorporated herein by reference: U.S. Pat. No. 8,483,830 to Tweden et al/issued Jul. 9, 2013; U.S. Pat. No. 7,167,750 to Knudson et al. issued Jan. 23, 2007; US 2005/0131485 A1 published Jun. 16, 2005, US 2005/0038484 A1 published Feb. 17, 2005, US 2004/0172088 A1 published Sep. 2, 2004, US 2004/0172085 A1 published Sep. 2, 2004, US 2004/0176812 A1 published Sep. 9, 2004 and US 2004/0172086 A1 published Sep. 2, 2004. Also incorporated herein by reference is International patent application Publication No. WO 2006/023498 A1 published Mar. 2, 2006.

Conditions Associated with Impaired Glucose Regulation

The body converts the carbohydrates from food into glucose, a simple sugar that serves as a vital source of energy. The hormones insulin and glucagon play an important role in glucose regulation. The pancreas contains a collection of cells called the Islet of Langerhans which releases both insulin and glucagon. When the body does not convert enough glucose, blood sugar levels remain high. The pancreas secretes insulin to help the cells absorb glucose, reducing blood sugar and providing the cells with glucose for energy. When blood glucose falls, cells in the pancreas secrete glucagon. Glucagon instructs the liver to convert stored glucose (i.e. glycogen) to glucose, making glucose more available in the bloodstream. Insulin and glucagon work in a cycle. Glucagon interacts with the liver to increase blood sugar, while insulin reduces blood sugar by helping the cells use glucose.

Conditions associated with impaired glucose regulation include Type 2 diabetes, impaired glucose tolerance, impaired fasting glucose, gestational diabetes, and Type 1 diabetes. "Impaired glucose regulation" refers to alterations in one or more of glucose absorption, glucose production, insulin secretion, insulin sensitivity, GLP-1 regulation, and glucagon regulation.

Type 2 diabetes is a disease in which liver, muscle and fat cells do not use insulin properly to import glucose into the cells and provide energy to the cells. As the cells begin to starve for energy, signals are sent to the pancreas to increase insulin production. In some cases, the pancreas eventually produces less insulin exacerbating the symptoms of high blood sugar. Patients with Type 2 diabetes have a fasting blood (plasma) glucose of 126 mg/dL or greater; oral glucose tolerance of 200 mg/dL or greater; and/or percentage of HbA1C of 6.5% or greater. In some cases, the HbA1C percentage is 6-7%, 7-8%, 8-9%, 9-10%, and greater than 10%.

Despite the presence of treatments for type 2 diabetes, not all patients achieve glucose control or maintain glucose control. A patient that has not achieved glycemic control will typically have an HbA1C of greater than 7%. In some embodiments, patients are selected that continue to have problems with glycemic control even with drug treatment.

Patients with impaired glucose tolerance and/or impaired fasting glucose are those patients that have evidence of some minimal level of lack of glucose control. Patients can be naïve to any treatment or are those that have been treated with one or more pharmaceutical treatments. "Pre-Diabetes" is a term that is used by the American Diabetes Association to refer to people who have a higher than normal blood glucose but not high enough to meet the criteria for diabetes. The lack of glycemic control can be determined by the fasting plasma glucose test (FPG) and/or the oral glucose tolerance test (OGTT). The blood glucose levels measured after these tests determine whether the patient has normal glucose metabolism, impaired glucose tolerance, impaired fasting glucose, or diabetes. If the patient's blood glucose level is abnormal within a specified range following the FPG, it is referred to as impaired fasting glucose (IFG); if the patient's glucose level is abnormal within a specified range following the OGTT, it is referred to as impaired glucose tolerance (IGT). A patient is identified as having impaired fasting glucose with a FPG of greater than equal to 100 to less than 126 mg/dL and/or impaired glucose tolerance with an OGTT of greater than or equal to 140 to less that 200 mg/dL. A person with Pre-Diabetes can have IFG and/or IGT in those ranges.

In some embodiments, patients are selected that are overweight but not obese (have a BMI less than 30) and have Type 2 diabetes, that are overweight but not obese and have Pre-diabetes, or that have Type 2 diabetes and are not overweight or obese. In some embodiments, patients are selected that have one or more risk factors for Type 2 diabetes. These risk factors include age over 30, family history, overweight, cardiovascular disease, hypertension, elevated triglycerides, history of gestational diabetes, IFG, and/or IGT.

This disclosure includes systems and methods for treating impaired glucose regulation in a subject. In embodiments, a method of treating a condition associated with impaired glucose regulation in a subject comprises applying an intermittent (or continuous) electrical signal to a target nerve of the subject, with the electrical signal selected to down-regulate neural activity on the nerve and to restore neural activity on the nerve upon discontinuance of the block. In some embodiments, the target nerve is the vagus nerve. In some embodiments, the site on the target nerve is located to avoid affecting heart rate such as below the vagal enervation of the heart. In some embodiments, the electrical signal is selected for frequency, amplitude, pulse width, and timing.

The electrical signal may also be further selected to improve glucose regulation. Improvement of glucose regulation can be determined by a change in any one of % of HbA1C, fasting glucose, or glucose tolerance test (IVGTT). In some embodiments, the method further comprises combining the application of an electrical signal treatment with administration of an agent that affects glucose regulation. In some embodiments, the application of the electrical signal treatment excludes application of an electrical signal treatment to other nerves or organs.

In some aspects of the disclosure, a method and system comprises modulating the amount and/or secretion of glucagon, or insulin by application of a neural conduction block, or by application of neural stimulation, or a combination of both as described herein in order to facilitate glucose regulation.

In some embodiments, a method and system comprises applying an intermittent (or continuous) electrical signal to a target nerve or organ of the subject, with said electrical signal selected to down-regulate neural activity on the nerve and to restore neural activity on the nerve upon discontinuance of said signal; and applying a second intermittent (or continuous) electrical signal to a second target nerve or organ of the subject, with said electrical signal selected to up-regulate or down-regulate neural activity on the nerve and to restore neural activity on the nerve upon discontinuance of said signal.

In embodiments, the first target nerve is selected from the group consisting of the ventral vagus nerve, the hepatic branch of the vagus nerve, the celiac branch of the vagus nerve, and the dorsal vagus nerve. In at least these embodiments, the second target nerve can include the celiac branch of the vagus nerve, nerves of the duodenum, jejunum, small bowel, colon and ileum, and sympathetic nerves enervating the gastrointestinal tract. In some embodiments, the first target organ can include the stomach, esophagus, and liver. In some embodiments, the second target organ can include the spleen, pancreas, duodenum, small bowel, jejunum, colon, or ileum.

In some embodiments a down regulating signal may be applied to a target nerve such as the ventral vagus nerve and the upregulating signal applied to a second target nerve such as the splanchnic or the celiac branch of the vagus nerve. In some embodiments, the upregulating signal can be applied to an electrode positioned on an organ such as pancreas, spleen, duodenum, small bowel, jejunum, colon, or ileum and a downregulating signal applied to a hepatic branch of the vagus nerve. In other embodiments, stimulation of the vagus nerve celiac branch alone, or dorsal vagal trunk above the branching point of the celiac, causes a significant increase in blood glucose in 5 minutes or less. However, continuous stimulation is not be ideal due to complications of hyperglycemia. A system that monitors blood glucose levels and then initiates, or adjusts, vagus nerve stimulation when blood glucose decreases to an unsafe level is more desirable. In some embodiments, the upregulating signal may be applied in response to detecting an increase in blood glucose. Detection of blood glucose is achieved, for example, be using a glucose monitor in communication with the neuromodulator system.

A. Description of Vagal Innervation of the Alimentary Tract

FIG. 1 is a schematic illustration of an alimentary tract (GI tract plus non-GI organs such as the pancreas and gall bladder (pancreas, liver, and gall bladder are considered GI organs), collectively labeled PG) and its relation to vagal and enteric innervation. The lower esophageal sphincter (LES) acts as a gate to pass food into the stomach S and, assuming adequate function of all components, prevent reflux. The pylorus PV controls passage of chyme from the stomach S into the intestines I (collectively shown in the figures and including the large intestine or colon and the small intestine including the duodenum, jejunum and ileum). The biochemistry of the contents of the intestines I is influenced by the pancreas P and gall bladder PG which discharge into the duodenum. This discharge is illustrated by dotted arrow A.

Figure 2:
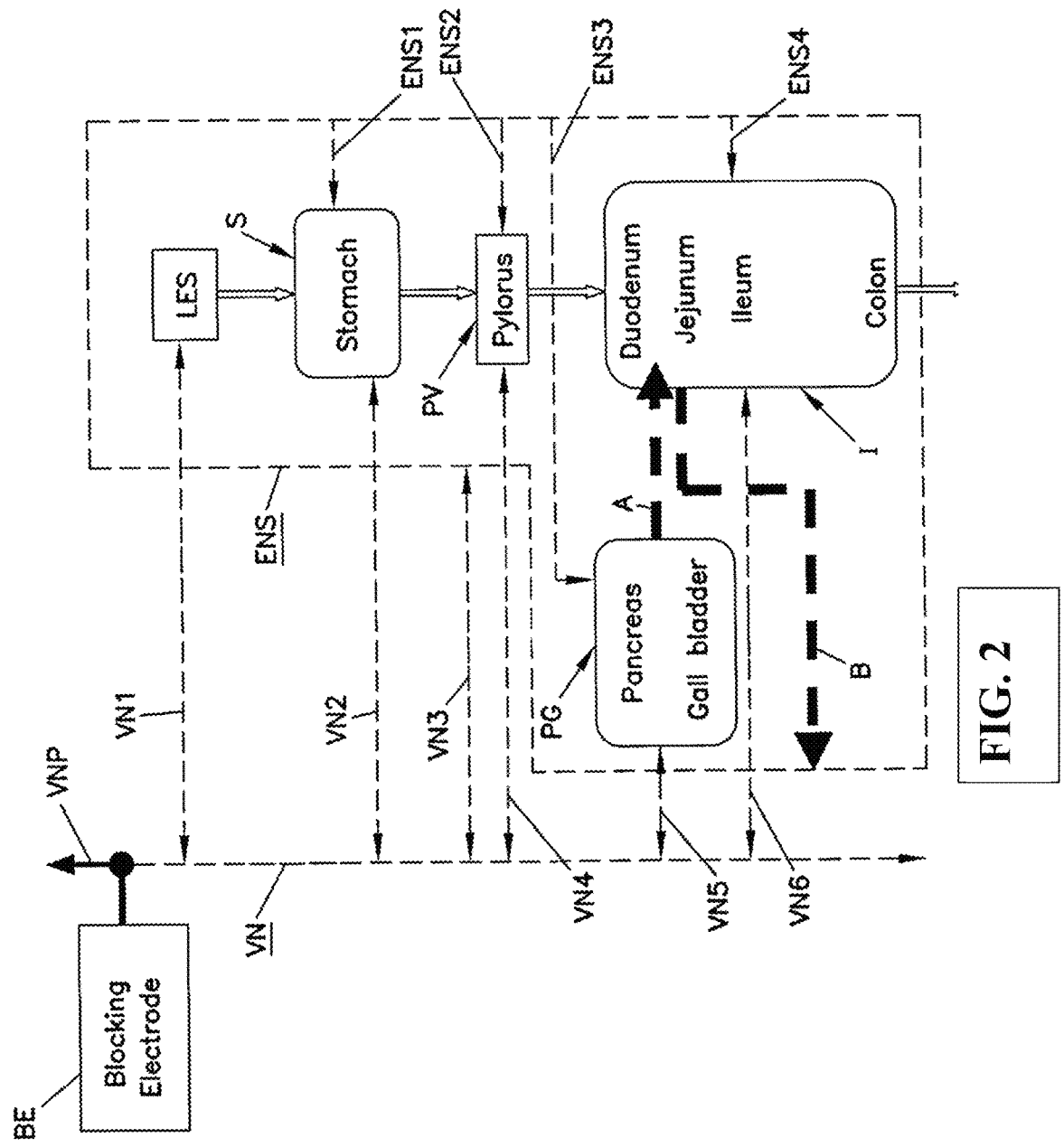
FIG. 2 is the view of FIG. 1 showing the application of a blocking electrode to the alimentary tract.

The vagus nerve VN transmits signals to the stomach S, pylorus PV, pancreas and gall bladder PG directly. Originating in the brain, there is a common vagus nerve VN in the region of the diaphragm (not shown). In the region of the diaphragm, the vagus VN separates into ventral and dorsal components with both acting to innervate the GI tract. In FIGS. 1, and 2, the ventral and dorsal vagus nerves are not shown separately. Instead, the vagus nerve VN is shown schematically to include both ventral and dorsal nerves. The vagus nerve VN contains both afferent and efferent components sending signals to and away from, respectively, its innervated organs.

Figure 6:
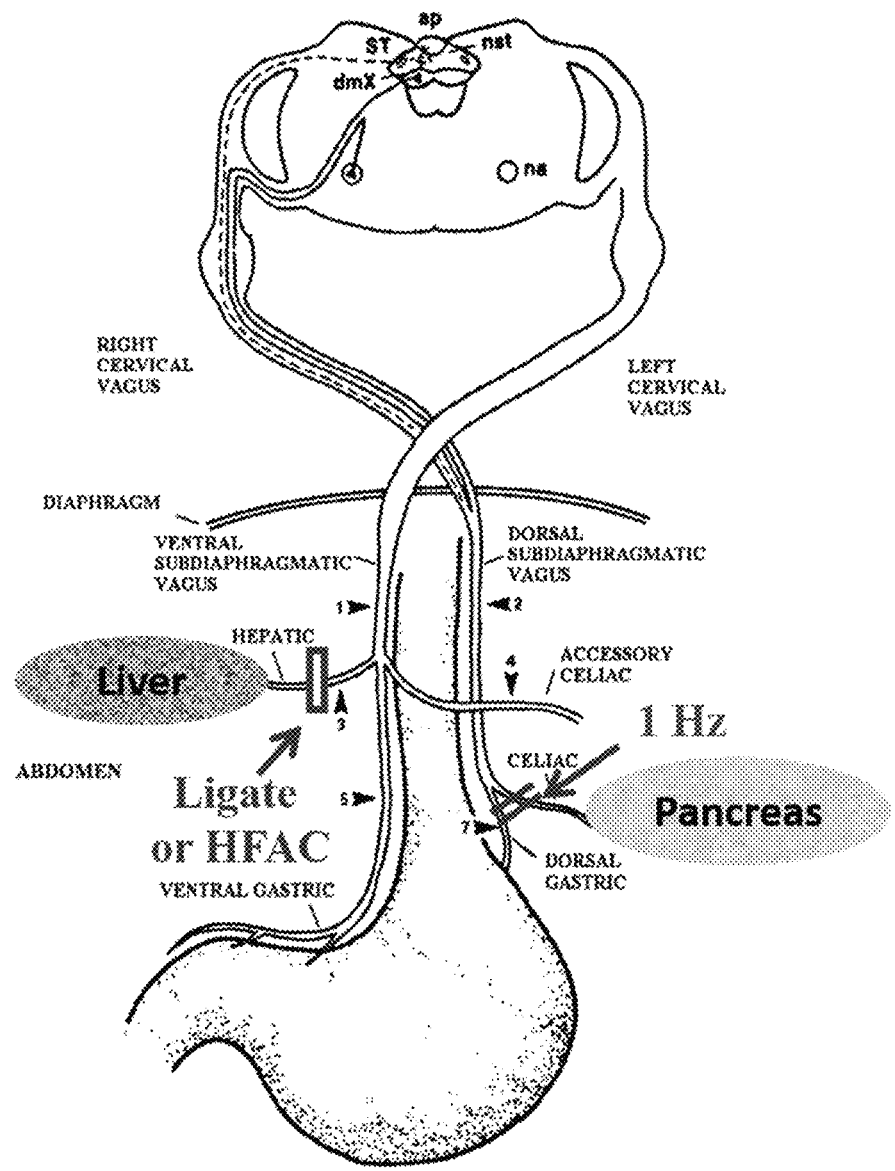
FIG. 6 depicts a device is shown for application of signals to different vagal nerve branches. A blocking or HFAC signal is applied to the hepatic branch of the anterior or ventral vagal nerve and the a stimulating signal is applied to the celiac branch of the posterior or dorsal vagal nerve.

The vagus nerve also includes the hepatic branch and the celiac nerve, best shown in FIG. 6. The hepatic branch is involved in providing signals regarding glucose production in the liver. The celiac nerve or branch is formed by contributions from the greater splanchnic and vagus (especially the dorsal or right vagus).

Referring again to FIGS. 1 and 2, in addition to influence from the vagus nerve VN, the GI and alimentary tracts are greatly influenced by the enteric nervous system ENS. The enteric nervous system ENS is an interconnected network of nerves, receptors and actuators throughout the GI tract and pancreas and gall bladder PG. There are many millions of nerve endings of the enteric nervous system ENS in the tissues of the GI organs. For ease of illustration, the enteric nervous system ENS is illustrated as a line enveloping the organs innervated by the enteric nervous system ENS. The vagus nerve VN innervates, at least in part, the enteric nervous system ENS (schematically illustrated by vagal trunk VN3 which represents many vagus-ENS innervation throughout the gut). Also, receptors in the intestines I connect to the enteric nervous system ENS. Arrow B in the figures illustrates the influence of duodenal contents on the enteric nervous system ENS as a feedback to the secretion function of the pancreas, liver and gall bladder. Specifically, receptors in the intestine I respond to the biochemistry of the intestine contents (which are chemically modulated by the pancreao-biliary output of Arrow A). This biochemistry includes pH and osmolality.

In FIGS. 1 and 2, vagal trunks VN1, VN2, VN4 and VN6 illustrate schematically the direct vagal innervation of the GI organs of the LES, stomach S, pylorus PV and intestines I. Trunk VN3 illustrates direct communication between the vagus VN and the ENS. Trunk VN5 illustrates direct vagal innervation of the pancreas and gall bladder. Enteric nerves ENS1-ENS4 represent the multitude of enteric nerves in the stomach S, pylorus PV, pancreas and gall bladder PG and intestines I.

While communicating with the vagus nerve VN, the enteric nervous system ENS can act independently of the vagus and the central nervous system. For example, in patients with a severed vagus nerve (vagotomy—a historical procedure for treating ulcers), the enteric nervous system can operate the gut. Most enteric nerve cells are not directly innervated by the vagus.

B. Therapy Delivery Equipment

The disclosure provides systems and devices for treating a condition associated with impaired glucose regulation comprising a pulse generator that provides signals to modulate neural activity on a target nerve or organ.

In embodiments, a system comprises at least two electrodes operably connected to an implantable pulse generator, wherein one of the electrodes is adapted to be placed on a target nerve; an implantable pulse generator that comprises a power module and a programmable therapy delivery module, wherein the programmable therapy delivery module is configured to deliver at least one therapy program comprising an electrical signal treatment applied intermittently multiple times in a day and over multiple days to the target nerve, wherein the electrical signal has a frequency selected to downregulate and/or upregulate activity on the target nerve and has an on time and an off time, wherein the off time is selected to allow at least a partial recovery of the activity of the target nerve; and an external component comprising an antenna and a programmable storage and communication module, wherein programmable storage and communication module is configured to store the at least one therapy program and to communicate the at least one therapy program to the implantable pulse generator.

In an embodiment, a system (schematically shown in FIG. 3) for treating such conditions as diabetes or prediabetes includes a pulse generator 104, an external mobile charger 101, and two electrical lead assemblies 106, 106a. The pulse generator 104 is adapted for implantation within a patient to be treated. In some embodiments, the pulse generator 104 is implanted just beneath a skin layer 103. In related embodiments the system includes 1 or more pulse generators 104.

In some embodiments, the lead assemblies 106, 106a are electrically connected to the circuitry of the pulse generator 104 by conductors 114, 114a. Industry standard connectors 122, 122a are provided for connecting the lead assemblies 106, 106a to the conductors 114, 114a. As a result, leads 116, 116a and the pulse generator 104 may be separately implanted. Also, following implantation, lead 116, 116a may be left in place while the originally placed pulse generator 104 is replaced by a different pulse generator.

The lead assemblies 106, 106a up-regulate and/or down-regulate nerves of a patient based on the therapy signals provided by the neuroregulator 104. In an embodiment, the lead assemblies 106, 106a include distal electrodes 212, 212a, which are placed on one or more nerves or organs of a patient. For example, the electrodes 212, 212a may be individually placed on the celiac nerve, the vagal nerve, the hepatic branches of the vagal nerve, or some combination of these, respectively, of a patient. For example, the leads 106, 106a have distal electrodes 212, 212a which are individually placed on the ventral and dorsal vagal nerves VVN, DVN, respectively, of a patient, for example, just below the patient's diaphragm. By way of another example FIG. 6 shows leads placed on the hepatic branch and the celiac nerve. Fewer or more electrodes can be placed on or near fewer or more nerves. In some embodiments, the electrodes are cuff electrodes.

The external mobile charger 101 includes circuitry for communicating with the implanted neuroregulator (pulse generator) 104. In some embodiments, the communication is a two-way radiofrequency (RF) signal path across the skin 103 as indicated by arrows A. Example communication signals transmitted between the external charger 101 and the neuroregulator 104 include treatment instructions, patient data, and other signals as will be described herein. Energy or power also can be transmitted from the external charger 101 to the neuroregulator 104 as will be described herein.

In the example shown, the external charger 101 can communicate with the implanted neuroregulator 104 via bidirectional telemetry (e.g. via radiofrequency (RF) signals). The external charger 101 shown in FIG. 3 includes a coil 102, which can send and receive RF signals. A similar coil 105 can be implanted within the patient and coupled to the neuroregulator 104. In an embodiment, the coil 105 is integral with the neuroregulator 104. The coil 105 serves to receive and transmit signals from and to the coil 102 of the external charger 101.

For example, the external charger 101 can encode the information as a bit stream by amplitude modulating or frequency modulating an RF carrier wave. The signals transmitted between the coils 102, 105 preferably have a carrier frequency of about 6.78 MHz. For example, during an information communication phase, the value of a parameter can be transmitted by toggling a rectification level between half-wave rectification and no rectification. In other embodiments, however, higher or lower carrier wave frequencies may be used.

In an embodiment, the neuroregulator 104 communicates with the external charger 101 using load shifting (e.g., modification of the load induced on the external charger 101). This change in the load can be sensed by the inductively coupled external charger 101. In other embodiments, however, the neuroregulator 104 and external charger 101 can communicate using other types of signals.

In an embodiment, the neuroregulator 104 receives power to generate the therapy signals from an implantable power source 151 such as a battery. In a preferred embodiment, the power source 151 is a rechargeable battery. In some embodiments, the power source 151 can provide power to the implanted neuroregulator 104 when the external charger 101 is not connected. In other embodiments, the external charger 101 also can be configured to provide for periodic recharging of the internal power source 151 of the neuroregulator 104. In an alternative embodiment, however, the neuroregulator 104 can entirely depend upon power received from an external source. For example, the external charger 101 can transmit power to the neuroregulator 104 via the RF link (e.g., between coils 102, 105).

In some embodiments, the neuroregulator 104 initiates the generation and transmission of therapy signals to the lead assemblies 106, 106a. In an embodiment, the neuroregulator 104 initiates therapy when powered by the internal battery 151. In other embodiments, however, the external charger 101 triggers the neuroregulator 104 to begin generating therapy signals. After receiving initiation signals from the external charger 101, the neuroregulator 104 generates the therapy signals (e.g., pacing signals) and transmits the therapy signals to the lead assemblies 106, 106a.

In other embodiments, the external charger 101 also can provide the instructions according to which the therapy signals are generated (e.g., pulse-width, amplitude, and other such parameters). In some embodiments, the external component comprises an communication system and a programmable storage and communication module. Instructions for one or more therapy programs can be stored in the programmable storage and communication module. In a preferred embodiment, the external charger 101 includes memory in which several predetermined programs/therapy schedules can be stored for transmission to the neuroregulator 104. The external charger 101 also can enable a user to select a program/therapy schedule stored in memory for transmission to the neuroregulator 104. In another embodiment, the external charger 101 can provide treatment instructions with each initiation signal.

Typically, each of the programs/therapy schedules stored on the external charger 101 can be adjusted by a physician to suit the individual needs of the patient. For example, a computing device (e.g., a notebook computer, a personal computer, etc.) 100 can be communicatively connected to the external charger 101. With such a connection established, a physician can use the computing device 107 to program therapies into the external charger 101 for either storage or transmission to the neuroregulator 104.

The neuroregulator 104 also may include memory in which treatment instructions and/or patient data can be stored. In some embodiments, the neuroregulator comprises a power module and a programmable therapy delivery module. For example, the neuroregulator 104 can store one or more therapy programs in the programmable therapy delivery module indicating what therapy should be delivered to the patient. The neuroregulator 104 also can store patient data indicating how the patient utilized the therapy system and/or reacted to the delivered therapy.

In some embodiments, the external component and/or the neuroregulator, are programmed with one or more therapy programs. One therapy program may comprise an electrical signal treatment applied intermittently multiple times in a day and over multiple days, wherein the electrical signal has a frequency selected to downregulate activity on the target nerve and has an on time and an off time, wherein the off time is selected to allow at least a partial recovery of the activity of the target nerve. Another therapy program may comprise an electrical signal treatment applied continuously over multiple days, wherein the electrical signal has a frequency selected to downregulate or upregulate activity on the target nerve. A second therapy program may comprise an electrical signal treatment applied intermittently multiple times in a day and over multiple days, wherein the electrical signal has a frequency selected to upregulate or down regulate activity on second target nerve or organ, and has an on time and an off time, wherein the off time is selected to allow at least a partial recovery of the activity of the target nerve. The first and/or second therapy programs may be applied at the same time, at different times, or at overlapping times. The first and/or second therapy programs may be delivered at specific times of the day, and or in response to a signal from a sensor. In some embodiments the sensor is designed to measure the blood glucose level of a patient. In some embodiments the off time is configured to commence upon the detection of blood glucose levels between 80 mg/dL and 110 mg/dL In some embodiment the on time is configured to commence upon the detection of blood glucose levels above 110 mg/mL, above 150 mg/dL, above 200 mg/dL, or above 400 mg/dL.

Figure 3:
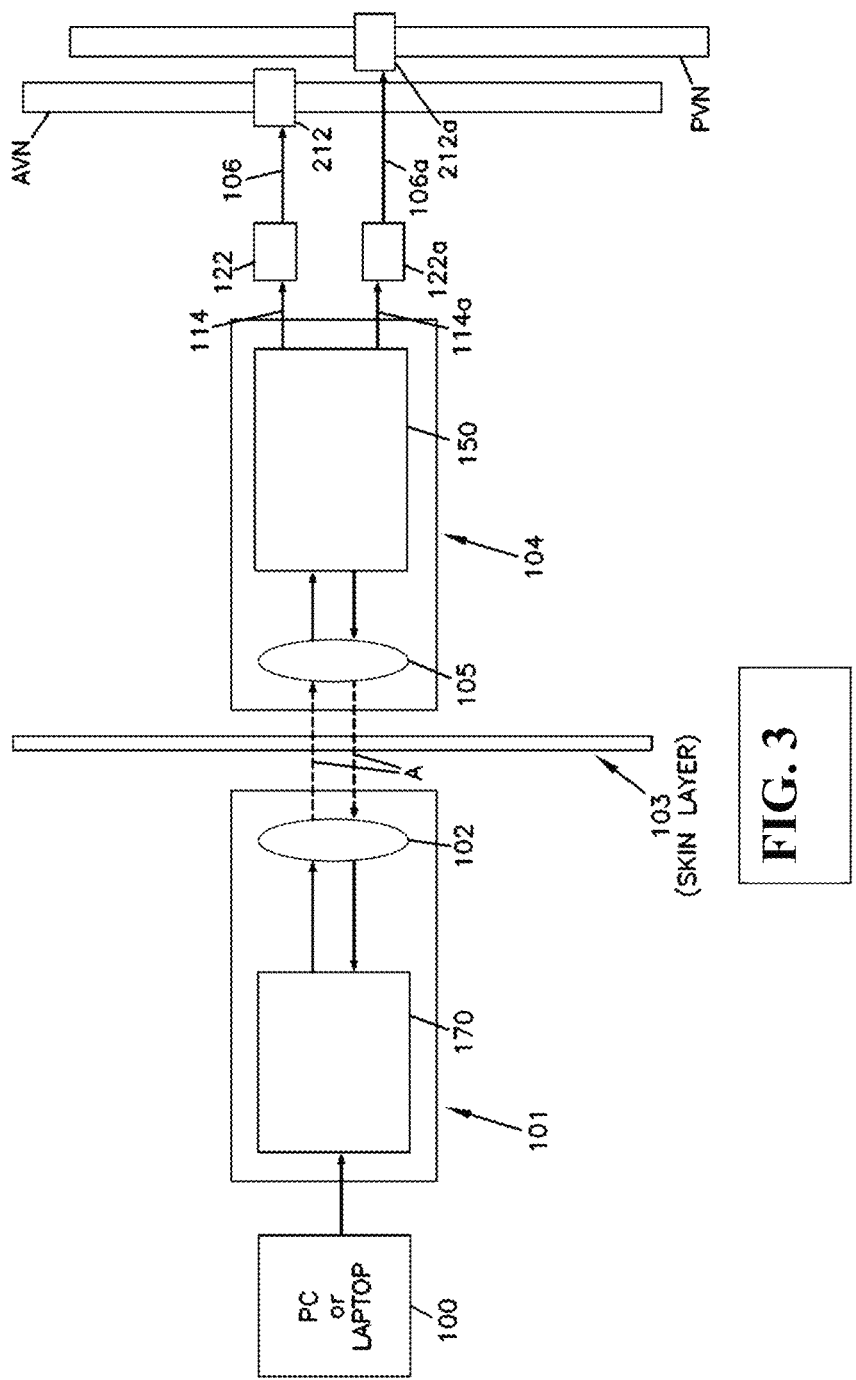
FIG. 3. is a schematic representation of an exemplary pulse generator and leads comprising electrodes placed on an anterior and posterior vagus nerve.

Referring to FIG. 3, the circuitry 170 of the external mobile charger 101 can be connected to an external coil 102. The coil 102 communicates with a similar coil 105 implanted within the patient and connected to the circuitry 150 of the pulse generator 104. Communication between the external mobile charger 101 and the pulse generator 104 includes transmission of pacing parameters and other signals as will be described.

Having been programmed by signals from the external mobile charger 101, the pulse generator 104 generates upregulating signals and/or downregulating signals to the leads 106, 106a. As will be described, the external mobile charger 101 may have additional functions in that it may provide for periodic recharging of batteries within the pulse generator 104, and also allow record keeping and monitoring.

While an implantable (rechargeable) power source for the pulse generator 104 is preferred, an alternative design could utilize an external source of power, the power being transmitted to an implanted module via the RF link (i.e., between coils 102, 105). In this alternative configuration, while powered externally, the source of the specific blocking signals could originate either in the external power source unit, or in the implanted module.

The electronic energization package may, if desired, be primarily external to the body. An RF power device can provide the necessary energy level. The implanted components could be limited to the lead/electrode assembly, a coil and a DC rectifier. With such an arrangement, pulses programmed with the desired parameters are transmitted through the skin with an RF carrier, and the signal is thereafter rectified to regenerate a pulsed signal for application as the stimulus to the vagus nerve to modulate vagal activity. This would virtually eliminate the need for battery changes.

However, the external transmitter must be carried on the person of the patient, which is inconvenient. Also, detection is more difficult with a simple rectification system, and greater power is required for activation than if the system were totally implanted. In any event, a totally implanted system is expected to exhibit a relatively long service lifetime, amounting potentially to several years, because of the relatively small power requirements for most treatment applications. Also, as noted earlier herein, it is possible, although considerably less desirable, to employ an external pulse generator with leads extending percutaneously to the implanted nerve electrode set. The major problem encountered with the latter technique is the potential for infection. Its advantage is that the patient can undergo a relatively simple procedure to allow short term tests to determine whether the condition associated with excess weight of this particular patient is amenable to successful treatment. If it is, a more permanent implant may be provided.

According to an embodiment of the invention, an apparatus is disclosed for applying an electrical signal to an internal anatomical feature of a patient. The apparatus includes at least one electrode for implantation within the patient and placement at the anatomical feature (e.g., a nerve) for applying the signal to the feature upon application of the signal to the electrode. An implantable component is placed in the patient's body beneath a skin layer and having an implanted circuit connected to the electrode. The implanted circuit includes an implanted communication system. An external component has an external circuit with an external communication system for placement above the skin and adapted to be electrically coupled to the implanted communication system across the skin through radiofrequency transmission. The external circuit has a plurality of user interfaces including an information interface for providing information to a user and an input interface for receiving inputs from the user.

Figure 4:
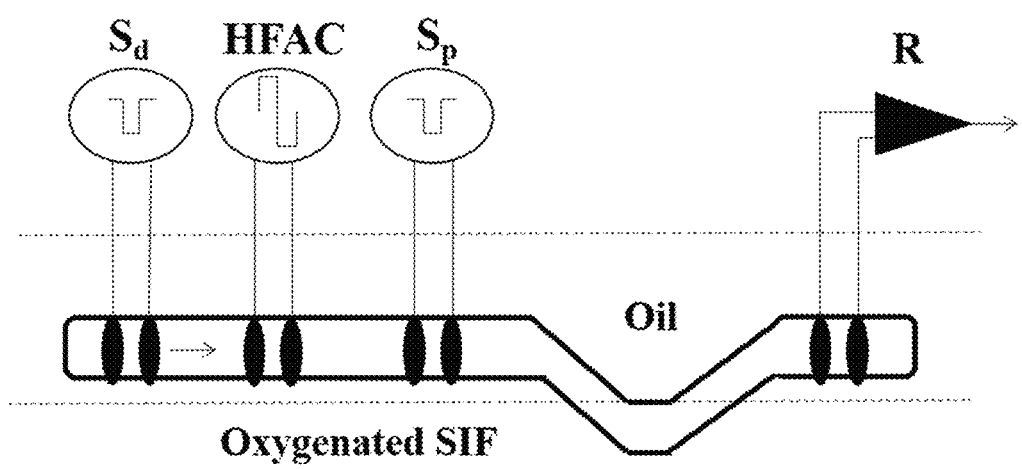
FIG. 4 is a schematic illustration of a design for isolated vagus nerve conduction blocking experiments.
Figure 5:
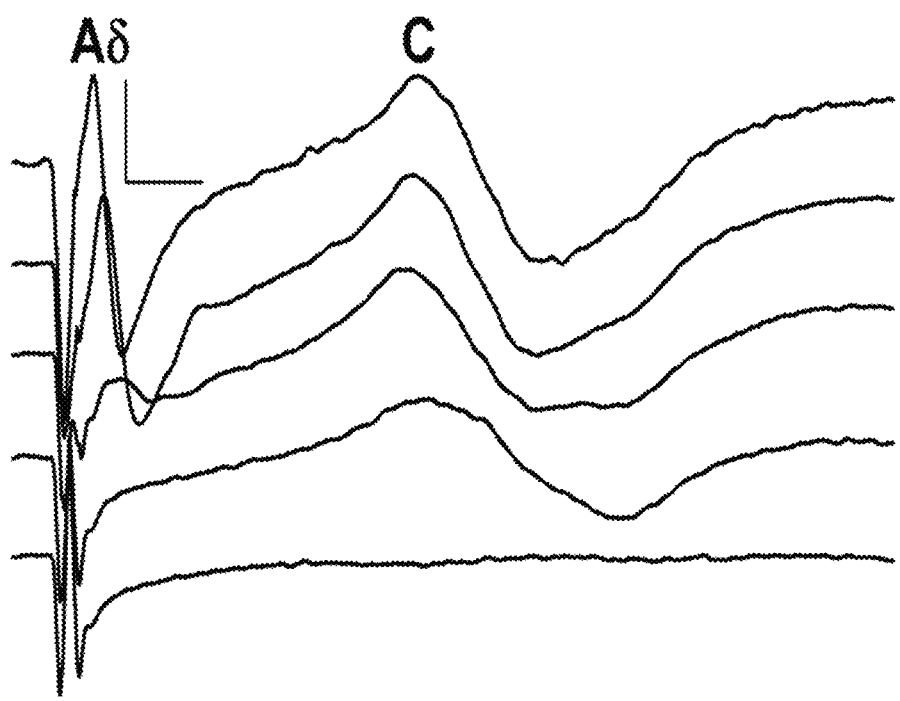
FIG. 5 is a graphical illustration of the degree of block is dependent on HFAC Amplitude.

As shown in FIG. 4 an isolated vagus nerve preparation was used to test the ability of high frequency pulse generator to block axon conduction. As shown, $S_d$ depicts the distal stimulation electrode, HFAC is the electrode delivering 5000 Hz, $S_p$ designates the proximal stimulation (Control) Electrode and R is the recording electrode. Referring now to FIG. 5, where the traces from top to bottom are compound action potentials (CAPs) evoked immediately following the application of 60 seconds at 5000 Hz at current amplitudes of 0, 3, 5, 8 and 10 mA. The faster $A\delta$ wave had a peak CV of 9.4 m s$^{-1}$. The slower C wave had a peak CV of 0.85 m s$^{-1}$. As shown, the $A\delta$ wave was fully blocked at a lower HFAC current amplitude (8 mA) then the C wave (10 mA). As shown in FIG. 5, the scale bar is 5 milliseconds by 200 µV.

As shown in FIG. 6 stimulation of the celiac branch of the vagal nerve can increase plasma insulin and glucagon. Ligation of the hepatic branches can decrease liver sensitivity to glucagon as well as decrease insulin resistance. Stimulation of vagus nerve fibers innervating the pancreas causes an increase in plasma insulin, however, blood glucose levels are either unchanged or increased. Blockade of neuronal fibers innervating the liver can also affect blood glucose possibly though disinhibition of vagal efferents innervating the pancreas, decreased hepatic sensitivity to glucagon and/or decreased insulin resistance through attenuation of PPARα. Little is known; however, of the effect on blood glucose with combined simulation of celiac fibers innervating the pancreas (increasing insulin secretion) and blockade of neuronal hepatic fibers innervating the liver in an animal model of Type 2 diabetes.

With reference to FIG. 6, a device is shown for application of signals to different vagal nerve branches. A stomach is shown schematically for the purpose of facilitating an understanding of applying a vagal nerve modulating signal. In FIG. 6, the esophagus passes through the diaphragm at an opening or hiatus. In the region where the esophagus passes through the diaphragm, trunks of the vagal nerve (illustrated as the ventral (anterior) vagus nerve (AVN) and dorsal (posterior) vagus nerve (PVN)) are disposed on opposite sides of the esophagus. It will be appreciated that the precise location of the ventral (anterior) and dorsal (posterior) vagus nerves AVN, PVN relative to one another and to the esophagus are subject to a wide degree of variation within a patient population. However, for most patients, the ventral and dorsal vagus nerves AVN, PVN are in close proximity to the esophagus at the hiatus where the esophagus passes through the diaphragm.

The ventral and dorsal vagus nerves AVN, PVN divide into a plurality of trunks that innervate organs such as the pancreas, gallbladder, liver, stomach, and intestines. Commonly, the ventral and dorsal vagus nerves AVN, PVN are still in close proximity to the esophagus and stomach (and not yet extensively branched out) at the region of the junction of the esophagus and stomach.

Figure 7:
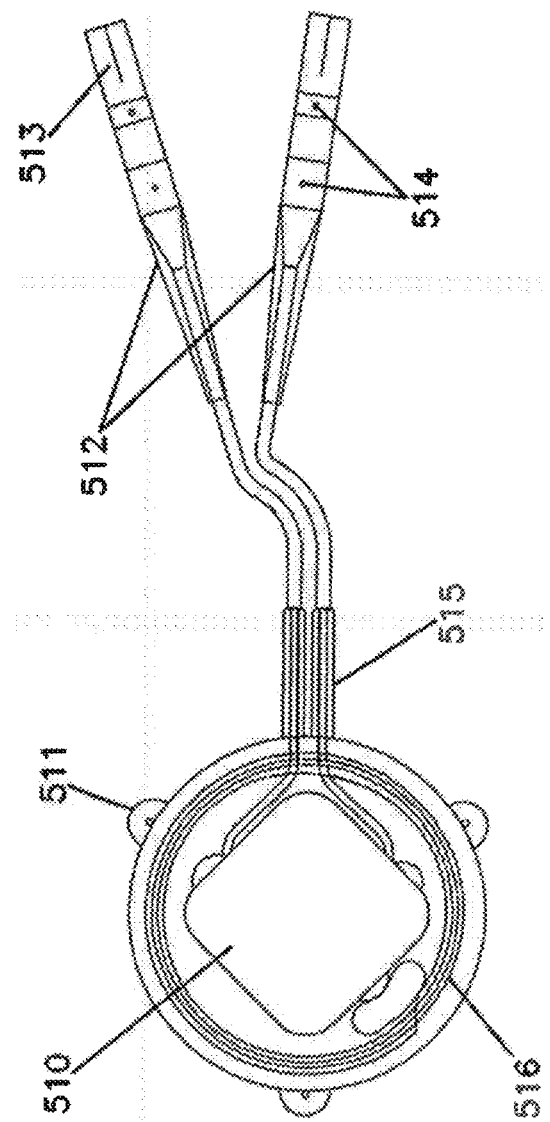
FIG. 7 illustrates a schematic representative of another exemplary embodiment comprising an implantable component.

Another embodiment of a device useful in treating a condition associated with impaired glucose regulation as described herein is shown in FIG. 7. With reference to FIG. 7, a device comprises an implantable component comprising an electronic assembly 510 ("hybrid circuit") and a receiving coil 516; standard connectors 512 (e.g. IS-1 connectors) for attachment to electrode leads. Two leads are connected to the IS-1 connectors for connection to the implanted circuit. Both have a tip electrode for placement on a nerve. Set screws are shown in 514 and allow for adjustment of the placement of the electrodes. In some embodiments, a marker 513 to indicate the dorsal or ventral lead is provided. Suture tabs 511 are provided to provide for implantation at a suitable site. In some embodiments, strain relief 515 is provided. The patient receives an external controller comprising an communication system connected to control circuitry. The external control unit can be programmed for various signal parameters including options for frequency selection, pulse amplitude and duty cycle.

In an embodiment, the nerves AVN, PVN are indirectly stimulated by passing electrical signals through the tissue surrounding the nerves. In some embodiments, the electrodes are bipolar pairs (i.e. alternating anode and cathode electrodes). In some embodiments, a plurality of electrodes may be placed overlying the ventral and/or dorsal vagus nerves AVN, PVN. As a result, energizing the plurality of electrodes will result in application of a signal to the ventral and dorsal vagus nerves AVN, PVN and/or their branches. In some therapeutic applications, some of the electrodes may be connected to a blocking electrical signal source (with a blocking frequency and other parameters as described below) and other electrodes may apply an upregulating signal. Of course, only a single array of electrodes could be used with all electrodes connected to a blocking or a downregulating signal. In some therapeutic applications, some of the electrodes may be connected to an up-regulating electrical signal source (with a suitable frequency and other parameters as described below).

In other embodiments, a plurality of electrodes are placed overlying the hepatic and celiac branches of the AVN, PVN nerves. In some therapeutic applications some of the electrodes may be connected to a blocking electrical signal source (with a blocking frequency and other parameters described below) and other electrodes may apply an upregulating signal. In some therapeutic application an electrode connected to a blocking electrical signal is placed on the hepatic branch of the vagal nerve. In other therapeutic applications an electrode connected to an upregulating signal is placed on the celiac branch. In still yet other therapeutic applications an first electrode connected to a blocking signal is placed on the hepatic branch and a second electrode, connected to an upregulating signal is place on the celiac branch. As shown in FIG. 6, in some therapeutic applications stimulation of the celiac branch has been shown to increase plasma insulin and glucagon, while down-regulation of the hepatic branches has been shown to decrease the livers sensitivity to glucagon as well as decrease insulin resistance.

The electrical connection of the electrodes to an pulse generator may be as previously described by having a leads (e.g. 106,106a) connecting the electrodes directly to an implantable pulse generator (eg. 104). Alternatively and as previously described, electrodes may be connected to an implanted communication system for receiving a signal to energize the electrodes.

Two paired electrodes may connect to a pulse generator for bi-polar signal. In other embodiments, a portion of the vagus nerve VN is dissected away from the esophagus E. An electrode is placed between the nerve VN and the esophagus E. Another electrode is placed overlying the vagus nerve VN on a side of the nerve opposite the first electrode and with electrodes axially aligned (i.e., directly across from one another). Not shown for ease of illustration, the electrodes may be carried on a common carrier (e.g., a PTFE or silicone cuff) surrounding the nerve VN. Other possible placements of electrodes are described herein US 2005/0131485 published Jun. 16, 2005, which patent publication is hereby incorporated by reference.

While any of the foregoing electrodes could be flat metal pads (e.g., platinum), the electrodes can be configured for various purposes. In an embodiment, an electrode is carried on a patch. In other embodiments, the electrode is segmented into two portions both connected to a common lead and both connected to a common patch. In some embodiments, each electrode is connected to a lead and placed to deliver a therapy from one electrode to another. A flexible patch permits articulation of the portions of the electrodes to relieve stresses on the nerve VN.

Neuroregulator (Pulse Generator)

The neuroregulator (pulse generator) generates electrical signals in the form of electrical pulses according to a programmed regimen. In embodiments, a blocking signal is applied as described herein.

The pulse generator utilizes a conventional microprocessor and other standard electrical and electronic components, and communicates with an external programmer and/or monitor by asynchronous serial communication for controlling or indicating states of the device. Passwords, handshakes and parity checks are employed for data integrity. The pulse generator also includes means for conserving energy, which is important in any battery operated device and especially so where the device is implanted for medical treatment of a disorder, and means for providing various safety functions such as preventing accidental reset of the device.

Features may be incorporated into the pulse generator for purposes of the safety and comfort of the patient. In some embodiments, the patient's comfort would be enhanced by ramping the application of the signal up during the first two seconds. The device may also have a clamping circuit to limit the maximum voltage (14 volts for example) deliverable to the vagus nerve, to prevent nerve damage. An additional safety function may be provided by implementing the device to cease signal application in response to manual deactivation through techniques and means similar to those described above for manual activation. In this way, the patient may interrupt the signal application if for any reason it suddenly becomes intolerable.

The intermittent (or continuous) aspect of the electrical signal treatment resides in applying the signal according to a prescribed duty cycle. The pulse signal is programmed to have a predetermined on-time in which a train or series of electrical pulses of preset parameters is applied to the vagus branches, followed by a predetermined off-time. Nevertheless, continuous application of the electrical pulse signal may also be effective. In some embodiments, the predetermined on time and off time is programmed to allow for at least partial recovery of the nerve to a state of non-down or up regulation.

Pulse generators, one supplying the hepatic vagus branch and the other the celiac vagus branch to provide the bilateral upregulation and/or downregulation may be used. Use of implanted pulse generator for performing the method of the invention is preferred, but treatment may conceivably be administered using external equipment on an outpatient basis, albeit only somewhat less confining than complete hospitalization. Implantation of one or more pulse generators, of course, allows the patient to be completely ambulatory, so that normal daily routine activities including on the job performance is unaffected.

The pulse generator may be programmed with programming wand and a personal computer using suitable programming software developed according to the programming needs and signal parameters which have been described herein. The intention, of course, is to permit noninvasive communication with the electronics package after the latter is implanted, for both monitoring and programming functions. Beyond the essential functions, the programming software should be structured to provide straightforward, menu-driven operation, HELP functions, prompts, and messages to facilitate simple and rapid programming while keeping the user fully informed of everything occurring at each step of a sequence. Programming capabilities should include capability to modify the electronics package's adjustable parameters, to test device diagnostics, and to store and retrieve telemetered data. It is desirable that when the implanted unit is interrogated, the present state of the adjustable parameters is displayed on the PC monitor so that the programmer may then conveniently change any or all of those parameters at the same time; and, if a particular parameter is selected for change, all permissible values for that parameter are displayed so that the programmer may select an appropriate desired value for entry into the pulse generator.

Other desirable features of appropriate software and related electronics would include the capability to store and retrieve historical data, including patient code, device serial number, number of hours of battery operation, number of hours of output, and number of magnetic activations (indicating patient intercession) for display on a screen with information showing date and time of the last one or more activations.

Diagnostics testing should be implemented to verify proper operation of the device, and to indicate the existence of problems such as with communication, the battery, or the lead/electrode impedance. A low battery reading, for example, would be indicative of imminent end of life of the battery and need for implantation of a new device. However, battery life should considerably exceed that of other implantable medical devices, such as cardiac pacemakers, because of the relatively less frequent need for activation of the pulse generator of the present invention. In any event, the nerve electrodes are capable of indefinite use absent indication of a problem with them observed on the diagnostics testing.

The device may utilize circadian or other programming as well, so that activation occurs automatically at normal mealtimes for this patient. This may be in addition to the provision for the manual, periodic between meal, and sensing-triggered activation as described above herein.

The pulse generator may also be activated manually by the patient by any of various means by appropriate implementation of the device. These techniques include the patient's use of an external magnet, or of an external RF signal generator, or tapping on the surface overlying the pulse generator, to activate the pulse generator and thereby cause the application of the desired modulating signal to the electrodes. Another form of treatment of may be implemented by programming the pulse generator to periodically deliver the vagal activity modulation productive of glycemic control at programmed intervals.

In some embodiments, the system may include one or more sensors that may provide for signals to initiate therapy signals to one or more electrodes. For example, a sensor may measure the amount of glucose in the blood and initiate an upregulating signal to a nerve or organ if the amount of blood glucose exceeds a certain threshold.

C. Methods

The disclosure provides methods of treating a subject for a condition associated with impaired glucose regulation. In some embodiments, a method comprises: applying an intermittent (or continuous) electrical signal to a target nerve at a site with said electrical signal selected to down-regulate and/or up-regulate neural activity on the nerve and with normal or baseline neural activity restoring upon discontinuance of said block or up-regulation. In embodiments, the method provides for an increase in secretion of glucagon, insulin, or both. In some embodiments, the methods further comprise administering a composition to the subject comprising an effective amount of an agent that increases glycemic control. In some embodiments, the electrical signal is applied to the nerve by implanting a device or system as described herein.

In some embodiments, a method of treating a condition associated with impaired glucose regulation in a subject comprises applying an intermittent (or continuous) neural conduction block to a target nerve of the subject having impaired glucose regulation at a blocking site with said neural conduction block selected to down-regulate neural activity on the nerve and to restore neural activity on the nerve upon discontinuance of said block.

In some embodiments methods include, treating a patient for diabetes or impaired glucose control with a concurrent treatment comprising: a) applying an intermittent (or continuous) neural block to a target nerve of the patient at multiple times per day and over multiple days with the block selected to down-regulate afferent and/or efferent neural activity on the nerve and with neural activity restoring upon discontinuance of said block; and b) applying an intermittent (or continuous) neural stimulation to a target nerve of the patient at multiple times per day and over multiple days with the stimulation selected to up-regulate afferent and/or efferent neural activity on the nerve with neural activity restoring upon discontinuance of said stimulation.

In other embodiments, a method of achieving glucose regulation in a patient comprises positioning an electrode on or near a vagus nerve branch, and an anodic electrode in contact with adjacent tissue; implanting a neurostimulator coupled to the electrodes into the patient, applying electrical pulses with defined characteristics of amplitude, pulse width, frequency and duty cycle to the vagus nerve branch wherein the defined characteristics are selected to improve glucose regulation in the patient.

In embodiments, the methods include a method of increasing or modifying the amount of glucagon, insulin, or both comprising: applying an intermittent (or continuous) electrical signal to a target nerve, with said electrical signal selected to up regulate or down-regulate neural activity on the nerve and to restore neural activity on the nerve upon discontinuance of said signal, wherein the electrical signal is selected to modify the amount of glucagon, insulin, or both. In some embodiments, the electrical signal is selected for frequency, pulse width, amplitude and timing to downregulate neural activity as described herein. In some embodiments, the electrical signal is selected for frequency, pulse width, amplitude and timing to upregulate neural activity as described herein. In some embodiments, the electrical signal is selected to modify release of glucagon and insulin by the pancreas. In some embodiments, the electrical signal is selected to increase insulin release, especially when blood glucose is elevated. In some embodiments, the electrical signal is selected to modify liver sensitivity to glucagon.

In embodiments, the electrical signal is applied intermittently in a cycle including an on time of application of the signal followed by an off time during which the signal is not applied to the nerve, wherein the on and off times are applied multiple times per day over multiple days. In some embodiments, the on time is selected to have a duration of about 30 seconds to about 5 minutes. When the signal is selected to downregulate activity on the nerve, the electrical signal is applied at a frequency of about 200 Hz to 10,000 Hz. When the signal is selected to upregulate activity on the nerve, the electrical signal is applied at a frequency of about 0.01 Hz up to 200 Hz.

In embodiments, the electrical signal is applied to an electrode positioned on the vagus nerve. In some cases, the electrical signal is applied on the hepatic branch of the vagus nerve. In other cases, the electrical signal is applied on the celiac branch of the vagus nerve. In some embodiments, the electrical signal is applied to an organ involved in glucose regulation such as the liver, pancreas, duodenum, jejunum, or ileum.

In embodiments, downregulating and upregulating signals are both applied. In some cases, the signals are applied at the same time, different times, or overlapping times. In some embodiments, a downregulating signal is applied to a vagus nerve near the liver, and an upregulating signal is applied to a vagus nerve near the pancreas. In some embodiments, a downregulating signal is applied to the hepatic branch of the vagus nerve, and an upregulating signal is applied to the celiac branch of the vagus nerve.

In some embodiments, a method of treating a condition associated with impaired glucose regulation in a subject comprises measuring blood glucose levels following an intravenous (IV) glucose tolerance test (IVGTT) during stimulation of the celiac branch of the vagus nerve and with ligation, or high frequency alternating current (HFAC) blockade, of the vagus nerve hepatic branch. Without being bound by theory it is believed that vagal nerve stimulation-induced pancreatic secretion of glucagon may explain why blood glucose was not attenuated in some embodiments of this disclosure.

In embodiments, the method further comprises detecting the level of blood glucose or insulin to determine whether to apply an electrical signal treatment. If the levels of blood glucose and/or insulin are increased to normal or baseline levels expected in a control sample from a subject without diabetes, treatment to increase glucagon and/or insulin may cease until the levels fall below the expected levels required to maintain adequate glucose control. Such levels are known or can be determined using methods known to those of skill in the art.

In embodiments, the method further comprises administering an agent that improves glucose control. Such agents include agents that increase the amount of insulin and/or increase the sensitivity of cells to insulin. Non-limiting examples of agents include insulin, insulin analogs, sulfonylureas, meglitinides, GLP-1 analogs, DPP4 inhibitors, and PPAR alpha, gamma, or delta agonists.

Signal Application

In one aspect of the disclosure a reversible intermittent (or continuous) modulating signal is applied to a target nerve or organ in order to downregulate and/or upregulate neural activity on the nerve.

In embodiments of the methods described herein a neural conduction block is applied to a target nerve at a site with said neural conduction block selected to down-regulate neural activity on the nerve and with neural activity restoring upon discontinuance of said signal. Systems for applying such a signal are been described U.S. Pat. No. 7,167,750; US2005/0038484 which is incorporated by reference.

In some cases, the nerve is a nerve that innervates one or more alimentary organs, including but not limited to the vagus nerve, celiac nerves, hepatic branch of the vagus nerve, and splanchnic nerve. The signal applied may upregulate and/or down regulate neural activity on one or more of the nerves.

In some embodiments, said modulating signal comprises applying an electrical signal. The signal is selected to down regulate or up regulate neural activity and allow for restoration of the neural activity upon discontinuance of the signal. A pulse generator, as described above, can be employed to regulate the application of the signal in order to alter the characteristic of the signal to provide a reversible intermittent (or continuous) signal. The characteristics of the signal include location of the signal, frequency of the signal, amplitude of the signal, pulse width of the signal, and the administration cycle of the signal. In some embodiments, the signal characteristics are selected to provide for improved glucose regulation.

In some embodiments, electrodes applied to a target nerve are energized with an intermittent (or continuous) blocking or down regulating signal. The signal is applied for a limited time (e.g., 5 minutes). The speed of neural activity recovery varies from subject to subject. However, 20 minutes is a reasonable example of the time needed to recover to baseline. After recovery, application of a blocking signal again down-regulates neural activity which can then recover after cessation of the signal. Renewed application of the signal can be applied before full recovery. For example, after a limited time period (e.g., 10 minutes) blocking can be renewed resulting in average neural activity not exceeding a level significantly reduced when compared to baseline. In some embodiments, the electrical signal is applied intermittently (or continuously) in a cycle including an on time of application of the signal followed by an off time during which the signal is not applied to the nerve, wherein the on and off times are applied multiple times per day over multiple days. In embodiments, the on and/or off times are selected to allow at least partial recovery of the nerve. While not meant to limit the disclosure, it is believed that allowing a recovery period for the nerve may avoid enteric accommodation.

Figure 8:
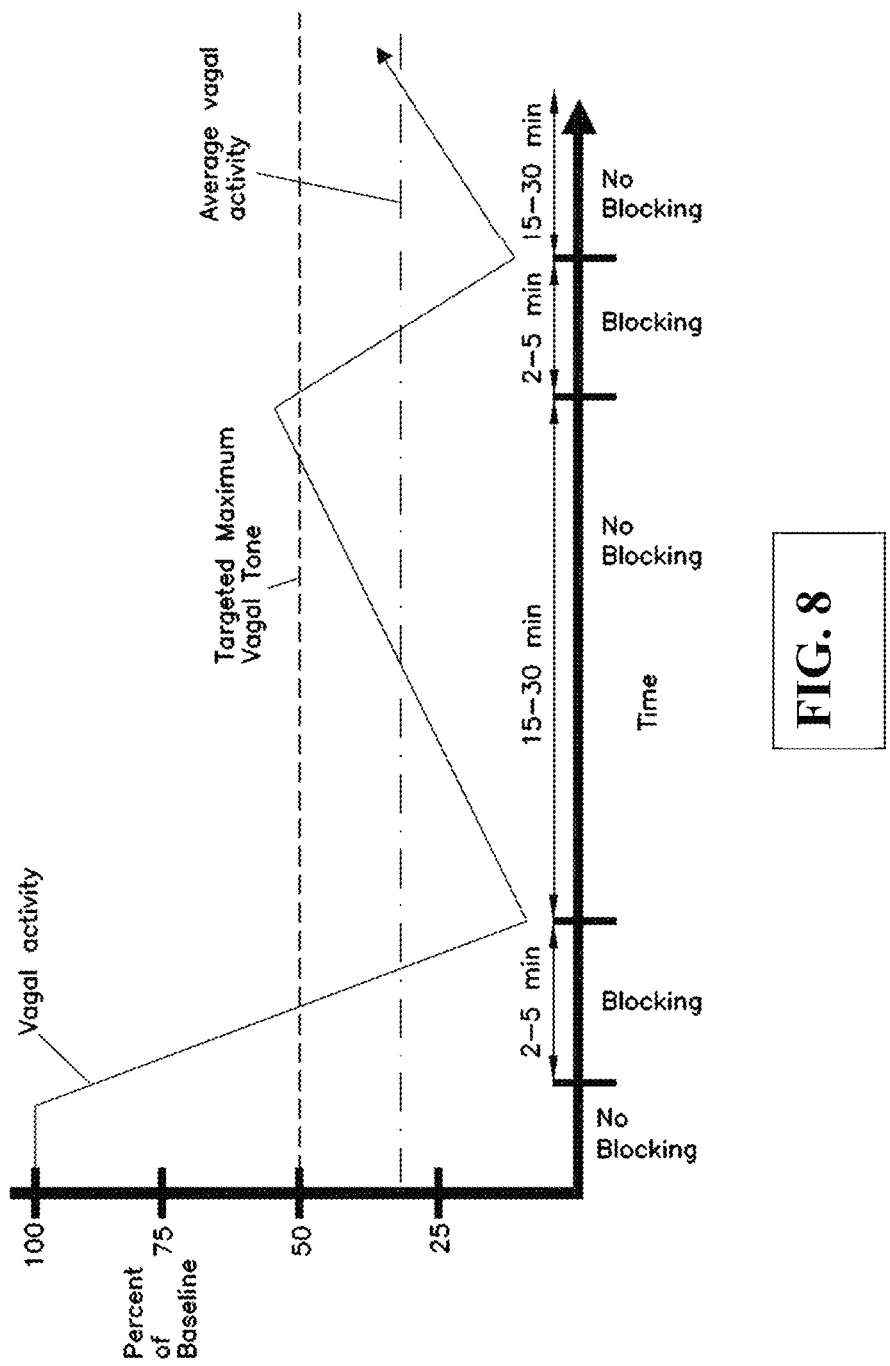
FIG. 8 shows recovery of the vagal nerve after application of blocking signal.

Recognition of recovery of neural activity, such as vagal activity, permits a treatment therapy and apparatus with enhanced control and enhanced treatment options. FIG. 8 illustrates vagal activity over time in response to application of a blocking signal as described above and further illustrates recovery of vagal activity following cessation of the blocking signal. It will be appreciated that the graph of FIG. 8 is illustrative only. It is expected there will be significant patient-to-patient variability. For example, some patients' responses to a blocking signal may not be as dramatic as illustrated. Others may experience recovery slopes steeper or shallower than illustrated. Also, vagal activity in some subjects may remain flat at a reduced level before increasing toward baseline activity. However, based on the aforementioned animal experiments, FIG. 8 is believed to be a fair presentation of a physiologic response to blocking.

In FIG. 8, vagal activity is illustrated as a percent of baseline (i.e., vagal activity without the treatment of the present invention). Vagal activity can be measured in any number of ways. For example, quantities of pancreatic exocrine secretion produced per unit time are an indirect measurement of such activity. Also, activity can be measured directly by monitoring electrodes on or near the vagus. Such activity can also be ascertained qualitatively (e.g., by a patient's sensation of bloated feelings or normalcy of gastrointestinal motility).

In FIG. 8, the vertical axis is a hypothetical patient's vagal activity as a percent of the patient's baseline activity (which varies from patient to patient). The horizontal axis represents the passage of time and presents illustrative intervals when the patient is either receiving a blocking signal as described or the blocking signal is turned off (labeled "No Blocking"). As shown in FIG. 8, during a short period of receiving the blocking signal, the vagal activity drops dramatically (in the example shown, to about 10% of baseline activity). After cessation of the blocking signal, the vagal activity begins to rise toward baseline (the slope of the rise will vary from patient to patient). The vagal activity can be permitted to return to baseline or, as illustrated in FIG. 8, the blocking signal can be re-instituted when the vagal activity is still reduced. In FIG. 8, the blocking signal begins when the vagal activity increases to about 50% of baseline. As a consequence, the average vagal activity is reduced to about 30% of the baseline activity. It will be appreciated that by varying the blocking time duration and the "no blocking" time duration, the average vagal activity can be greatly varied.

As described above and herein, the signal may be intermittent or continuous. The preferred nerve conduction block is an electronic block created by a signal at the vagus by an electrode controlled by the implantable pulse generator (such as pulse generator 104 or an external controller). The nerve conduction block can be any reversible block. For example, ultrasound, cryogenics (either chemically or electronically induced) or drug blocks can be used. An electronic cryogenic block may be a Peltier solid-state device which cools in response to a current and may be electrically controlled to regulate cooling. Drug blocks may include a pump-controlled subcutaneous drug delivery.

With such an electrode conduction block, the block parameters (signal type and timing) can be altered by pulse regulator and can be coordinated with the upregulating signals. As an illustrative example, the nerve conduction block is preferably within the parameters disclosed in Solomonow, et al., "Control of Muscle Contractile Force through Indirect High-Frequency Stimulation", Am. J. of Physical Medicine, Vol. 62, No. 2, pp. 71-82 (1983), which is incorporated herein by reference in its entirety. In some embodiments, the nerve conduction block is applied with electrical signal selected to block the entire cross-section of the nerve (e.g., both afferent, efferent, myelinated and non-myelinated fibers) at the site of applying the blocking signal (as opposed to selected sub-groups of nerve fibers or just efferent and not afferent or visa versa) and, more preferably, has a frequency selected to at least 200 Hz threshold frequency. Further, more preferred parameters are a frequency of 500 Hz (with other parameters, as non-limiting examples, being amplitude of 4 mA, pulse width of 0.5 msec, and duty cycle of 5 minutes on and 10 minutes off). In other related embodiments the signal blocking range is from 200 Hz to 10,000 Hz. As will be more fully described, the present embodiments give a physician great latitude in selecting stimulating and blocking parameters for individual patients.

In embodiments of the methods described herein a signal is applied to a target nerve at a site with said signal selected to up-regulate neural activity on the nerve and with neural activity restoring upon discontinuance of said signal. In some embodiments, an upregulating signal may be applied in combination with a down regulating signal in order to improve glucose regulation. For example, the upregulating signal may be applied to splanchnic nerve and/or celiac nerve.

The signal is selected to upregulate neural activity and allow for restoration of the neural activity upon discontinuance of the signal. A pulse generator, as described above, is employed to regulate the application of the signal in order to alter the characteristic of the signal to provide a reversible intermittent (or continuous) signal. The characteristics of the signal include frequency of the signal, location of the signal, and the administration cycle of the signal.

In some embodiments, electrodes applied to a target nerve are energized with an up regulating signal. The signal is applied for a limited time (e.g., 5 minutes). The speed of neural activity recovery varies from subject to subject. However, 20 minutes is a reasonable example of the time needed to recover to baseline. After recovery, application of an up signal again up-regulates neural activity which can then recover after cessation of the signal. Renewed application of the signal can be applied before full recovery. For example, after a limited time period (e.g., 10 minutes) upregulating signal can be renewed.

In some embodiments, an upregulating signal may be applied in combination with a down regulating signal in order to improve glucose regulation, increase/modify the amount and/or secretion of glucagon and/or insulin, and/or decrease the amount of blood glucose. The neural regulation signals can influence the sensitivity to glucagon by the liver, the amount of glucose absorbed from food, and the amount of glucagon and/or insulin secreted from the pancreas. The neural regulation provides for a decrease in the amount of insulin required by the subject.

The up-regulating and down-regulating signals may be applied to different nerves at the same time, applied to the same nerve at different times, or applied to different nerves at different times. In embodiments, an up-regulating signal may be applied to a celiac nerve or splanchnic nerve. In other embodiments, an up-regulating or downregulating signal may be applied to a hepatic branch of the vagus nerve or the signal may be applied to decrease the amount of glucose secreted from the liver.

In some embodiments, a downregulating signal is applied to a vagus nerve branch intermittently multiple times in a day and over multiple days in combination with an upregulating signal applied intermittently multiple times in a day and over multiple days to a different nerve or organ. In some embodiments, the upregulating signal is applied due to a sensed event such as the amount of blood glucose present. In other embodiments, an upregulating signal applied to the splanchnic nerve or the celiac nerve can be applied during a time period after normal meal times for the subject typically 15 to 30 minutes after mealtimes or times when blood glucose levels rise.

In some cases, signals are applied at specific times. For example, a downregulating signal may be applied before and during meal, followed by a stimulatory signal about 30 to 90 minutes after eating. In another example, a downregulating signal may be applied to the vagus nerve or the hepatic branch of the vagus nerve early in the morning when hepatic glucose is increasing.

In some embodiments, a stimulation signal is applied to the celiac branch of the vagus nerve when a monitor detects low blood glucose levels. In other embodiments a downregulating signal is continuously delivered to the hepatic branch of the vagus nerve, or the ventral vagal trunk above the branching point of the hepatic nerve, along with stimulation of the celiac branch, or the dorsal vagal trunk above the branching point of the celiac nerve. However, if an internal monitor detected blood glucose reaching an undesirable hypoglycemic state the blocking signal would cease and stimulation would continue alone.

In some embodiments, the signal parameters are adjusted to obtain an improvement in glucose regulation. An improvement, in glucose regulation can be determined by measurement of fasting glucose, oral glucose tolerance test, and/or the HbA1C or a decrease in the amount of insulin needed by the subject. In an embodiment, it is preferred that a reduction of the HbA1C in absolute percentage is at least 0.4% and more preferably is any % in the range of 0.4% to 5%. In some embodiments, a reduction of the HbA1C in absolute percentage is any one of 0.5%, 1%, 1.5%, 2%, 2.5%, 3%, 3.5%, 4%, 4.5%, or 5% or more. For example, a Type 2 diabetes patient may have a HbA1C of 9% and a reduction to HbA1C of 6.5% would be a reduction of 2.5% and would represent an improvement in glucose regulation.

In some embodiments, an improvement in glucose regulation comprises a fasting glucose of less than 126 mg/dL or greater and/or oral glucose tolerance of less than 200 mg/dL. In some embodiments the fasting glucose and/or oral glucose tolerance is reduced by at least 5% and more preferably any percentage in the range of 5 to 50%.

In an embodiment, an improvement in glucose regulation comprises one or more of the following characteristics: a HbA1C of less than or equal to 6.5%; less than 100 mg/dL fasting glucose; and/or less than 140 mg/dL oral glucose tolerance.

Location of Signal Application

Modulation of neural activity can be achieved by upregulating and/or down regulating neural activity of one or more target nerves or organs.

In some embodiments, electrodes can be positioned at a number of different sites and locations on or near a target nerve. Target vagus nerve branches include the celiac nerve, the hepatic nerve, the vagal nerve, the splanchnic nerve, or some combination of these, respectively, of a patient. The electrode may also be positioned to apply a signal to an organ in proximity to the vagus nerve such as the liver, duodenum, jejunum, ileum, spleen, pancreas, esophagus, or stomach. In some embodiments, the electrode is positioned to apply an electrical signal to the nerve at a location distal to the diaphragm of the subject.

Electrodes may be positioned on different nerves to apply a downregulating signal as opposed to an upregulating signal. For example, a down regulating signal can be applied on the hepatic nerve and an upregulating signal applied to the celiac nerve. In some embodiments, the signals may be applied to reduce the neurally mediated reflex secretion by blocking the vagal nerves to the liver, and concurrently or subsequently, stimulate the celiac to inhibit insulin secretion and/or upregulate the celiac nerve to stimulate glucagon production.

In some embodiments, the electrode is positioned to apply a signal to a branch or trunk of the vagus nerve. In other embodiments, the electrode is positioned to apply a signal to a ventral trunk, dorsal trunk or both. In some embodiments, the electrodes may be positioned at two different locations at or near the same nerve or on the nerve and on an alimentary tract organ.

For example, FIG. 2 illustrates placement of a blocking electrode. Referring to FIG. 2, the baseline vagal activity is illustrated by the solid line of the proximal vagus nerve segment VNP. The remainder of the vagus and enteric nervous system are shown in reduced thickness to illustrate down-regulation of tone. The pancreo-biliary output (and resulting feedback) is also reduced. In FIG. 2, the blocking electrode BE is shown high on the vagus relative to the GI tract innervation (e.g., just below the diaphragm), the sole blocking electrode could be placed lower (e.g., just proximal to pancreo/biliary innervation VN5). Blocking of the entire vagus as described above can be used to down-regulate the vagus for various benefits including treating a condition associated with impaired glycemic control. In some embodiments, the electrode may be placed on the celiac branch of the vagal nerve and provide for an upregulating signal. Other possible placements of electrodes are described herein US 2005/0131485 published Jun. 16, 2005, which patent publication is hereby incorporated by reference.

Signal Frequency and Timing

In some embodiments, a downregulating signal has a frequency of at least 200 Hz and up to 5000 Hz. In other embodiments, the signal is applied at a frequency of about 500 to 5000 Hz. Applicant has determined a most preferred blocking signal has a frequency of 3,000 Hz to 5,000 Hz or greater applied by two or more bi-polar electrodes. Such a signal has a preferred pulse width of 100 micro-seconds (associated with a frequency of 5,000 Hz). It is believed this frequency and pulse width best avoid neural recovery from blocking and avoid repolarization of the nerve by avoiding periods of no signal in the pulse cycle. A short "off" time in the pulse cycle (e.g., between cycles or within a cycle) could be acceptable as long as it is short enough to avoid nerve repolarization. The waveform may be a square or sinusoidal waveform or other shape. The higher frequencies of 5,000 Hz or more have been found, in porcine studies, to result in more consistent neural conduction block. Preferably, the signal is bi-polar, bi-phasic delivered to two or more electrodes on a nerve.

In some embodiments, a signal amplitude of 0.01 to 20.0 mA is adequate for blocking. In other embodiments a signal amplitude of 0.01 to 10 mA is adequate for blocking. In still yet other embodiments a signal amplitude of 0.01 to 8 mA is adequate for blocking. Other amplitudes may suffice. Other signal attributes can be varied to reduce the likelihood of accommodation by the nerve or an organ. These include altering the power, waveform or pulse width.

Upregulating signals typically comprise signals of a frequency of less than 200 Hz, more preferably between 0.01 to 200 Hz, more preferably 10 to 50 Hz, more preferably 5 to 20 Hz, more preferably 5 to 10 Hz, more preferably 1 to 5 Hz, preferably 0.1 to 2 Hz, most preferably 1 Hz. Such a signal has a preferred pulse width of 0.1-10 microseconds. In some embodiments, a signal amplitude of 0.1 to 12 mA is adequate for stimulating. Other amplitudes may suffice. Other signal attributes can be varied to reduce the likelihood of accommodation by the nerve or an organ. These include altering the power, waveform or pulse width.

Selection of a signal that upregulates and/or downregulates neural activity and/or allows for recovery of neural activity can involve selecting signal type and timing of the application of the signal. For example, with an electrode conduction block, the block parameters (signal type and timing) can be altered by the pulse generator and can be coordinated with the stimulating signals. The precise signal to achieve blocking may vary from patient to patient and nerve site. The precise parameters can be individually tuned to achieve neural transmission blocking at the blocking site.

In some embodiments, the signal has a duty cycle including an ON time during which the signal is applied to the nerve followed by an OFF time during which the signal is not applied to the nerve. For example, the on time and off times may be adjusted to allow for partial recovery of the nerve. In some cases, the downregulating and upregulating signals can be coordinated so that the upregulating signals are applied when down regulating signals are not being applied such as when the upregulating signals are applied at specific times or due to sensed events. In some embodiments, a sensed event indicates that an upregulating signal is applied and a down regulating signal is not applied for a time period relating to the sensed event, e.g. blood glucose exceeding a certain threshold. In preferred embodiments, the signal is continuously being applied.

In some embodiments, subjects receive an implantable component 104. (FIG. 3) The electrodes 212, 212a are placed on the anterior (ventral) vagus nerve AVN and posterior (dorsal) vagus nerve PVN just below the patient's diaphragm. The external antenna (coil 102) (or other communication system) is placed on the patient's skin overlying the implanted receiving coil 105. The external control unit 101 can be programmed for various signal parameters including options for frequency selection, pulse amplitude and duty cycle. For blocking signals, the frequency options include 2500 Hz and 5000 Hz (both well above a threshold blocking frequency of 200 Hz). The vast majority of treatments are 6-seconds at 5,000 Hz, alternating current signal, with a pulse width of 100 microseconds. The amplitude options are 0-10 mA. For stimulating signals, a frequency is selected of less than 200 Hz.

Duty cycle could also be controlled. A representative duty cycle is 5 minutes of on time followed by 5 minutes of no signal. The duty cycle is repeated throughout use of the device. In some embodiments, a mini duty cycle can be applied. In an embodiment, a mini duty cycle comprises 180 millisecond periods of mini-ON times of 5,000 Hz at a current which progressively increases from mini-ON time to mini-ON time until full current is achieved (or progressively decreases in the case of a ramp-down). Between each of such mini-ON times, there is a mini-OFF time which can vary but which is commonly about 20 milliseconds in duration during which no signal is applied. Therefore, in each 20-second ramp-up or ramp-down, there are approximately one hundred mini-duty cycles, having a duration of 200 milliseconds each and each comprising approximately 180 milliseconds of ON time and approximately 20 milliseconds of OFF time.

In some embodiments, an upregulating signal may be applied in combination with a down regulating signal in order to improve glucose regulation.

Normally a patient would only use the device while awake. The hours of therapy delivery can be programmed into the device by the clinician (e.g., automatically turns on at 7:00 AM and automatically turns off at 9:00 PM). In some cases, the hours of therapy would be modified to correspond to times when blood sugar fluctuates such as before a meal and 30-90 minutes after eating. For example, the hours of therapy may be adjusted to start at 5:00 AM before breakfast and end at 9:00 PM or later depending on when the last meal or snack is consumed. In the RF-powered version of the pulse generator, use of the device is subject to patient control. For example, a patient may elect to not wear the external antenna. The device keeps track of usage by noting times when the receiving antenna is coupled to the external antenna through radio-frequency (RF) coupling through the patient's skin.

In some embodiments, the external component 101 can interrogate the pulse generator component 104 for a variety of information. In some embodiments, therapy times of 30 seconds to 180 seconds per duty cycle are preferred to therapy times of less than 30 seconds per duty cycle or greater than 180 seconds per duty cycle.

During a 10 minute duty cycle (i.e., intended 5 minutes of therapy followed by a 5 minute OFF time), a patient can have multiple treatment initiations. For example, if, within any given 5-minute intended ON time, a patient experienced a 35-second ON time and 1.5 minute actual ON time (with the remainder of the 5-minute intended ON time being a period of no therapy due to signal interruption), the patient could have two actual treatment initiations even though only one was intended. The number of treatment initiations varies inversely with length of ON times experienced by a patient.

The flexibility to vary average neural activity, such as vagal activity, gives an attending physician great latitude in treating a patient. For example, in treating diabetes or prediabetes, the blocking signal can be applied with a short "no blocking" time. If the patient experiences discomfort due to dysmotility, the duration of the "no blocking" period can be increased to improve patient comfort. Also, the reduction of enzyme production can result in decreased fat absorption with consequential increase of fat in feces. The blocking and no blocking duration can be adjusted to achieve tolerable stool (e.g., avoiding excessive fatty diarrhea). The control afforded by the present invention can be used to prevent the enteric nervous system's assumption of control since vagal activity is not completely interrupted as in the case of a surgical and permanent vagotomy.

While patient comfort may be adequate as feedback for determining the proper parameters for duration of blocking and no blocking, more objective tests can be developed. For example, the duration of blocking and no blocking as well as combination with upregulating signals can be adjusted to achieve desired levels of glucose regulation. Such testing can be measured and applied on a per patient basis or performed on a statistical sampling of patients and applied to the general population of patients.

In some embodiments, a sensor may be employed. A sensing electrode SE can be added to monitor neural activity as a way to determine how to modulate the neural activity and the duty cycle. While sensing electrode can be an additional electrode to blocking electrode, it will be appreciated a single electrode could perform both functions. The sensing and blocking electrodes can be connected to a controller as shown in FIG. 3. Such a controller is the same as controller 102 previously described with the additive function of receiving a signal from sensing electrode.

In some embodiments, the sensor can be a sensing electrode, a glucose sensor, or sensor that senses other biological molecules or hormones of interest. When the sensing electrode SE yields a signal representing a targeted maximum vagal activity or tone (e.g., 50% of baseline as shown in FIG. 8) the controller with the additive function of receiving a signal from sensing electrode energizes the blocking electrode BE with a blocking signal. As described with reference to controller 102 (FIG. 3), controller with the additive function of receiving a signal from sensing electrode can be remotely programmed as to parameters of blocking duration and no blocking duration as well as targets for initiating a blocking signal or upregulating signal.

In some embodiments, of the apparatus and method described herein use recovery of the vagus nerve to control a degree of down-regulation of vagal activity. This gives a physician enhanced abilities to control a patient's therapy for maximum therapeutic effectiveness with minimum patient discomfort. Vagal neural blocking simulates a vagotomy but, unlike a vagotomy, is reversible and controllable.

EXAMPLES

The results herein show that electrical modulation of nerves innervating the pancreas and liver improves performance on an IVGTT in the Zucker obese (fatty) rat (ZDF fa/fa) model of Type 2 diabetes. In this study the celiac branch of the vagus nerve (innervating the pancreas) was stimulated simultaneously with either simultaneous ligation of the hepatic branch of the vagus nerve or application of HFAC to the hepatic nerve.

Zucker obese diabetic rats (ZDF fa/fa) (male ~300 grams), or Sprague Dawley control rats, were anesthetized with an IP injection of pentobarbital. Next, rats were placed on a heating blanket and the right jugular vein was cannulated. The depth of anesthesia was assessed with periodically testing a paw withdrawal reflex. If a reflex was observed a maintenance dose of pentobarbital was administered IV. Next, the abdominal cavity was opened and the liver retracted. The hepatic branch of the ventral vagus nerve and the celiac branch of the dorsal vagus nerve were isolated and separated from the esophagus.

Referring to FIGS. 10-13, the experimental protocol consisted of five experimental conditions: 1) Sham operation (nerve isolation only), 2) Vagotomy+Stimulation, 3) HFAC+Stimulation, 4) Vagotomy Alone and 5) Stimulation Alone. In the Vagotomy+Stimulation group the hepatic branch was ligated, and the celiac branch was stimulated at 1 Hz. In the HFAC+Stimulation group, the hepatic branch was blocked with 5000 Hz, and the celiac branch was stimulated at 1 Hz. In the Vagotomy Alone group the hepatic branch was ligated. In the Stimulation Alone group the celiac branch was stimulated at 1 Hz and the hepatic branch remained intact.

The 1 Hz stimulation consisted of a negative pulse (4 ms) generated by a Grass S44 stimulator (Grass Medical Instruments, Quincy, MA, USA) delivered through a constant current (8 mA) stimulus isolation unit (Model A360, World Precision Instruments, Sarasota, FL, USA). The HFAC (5000 Hz) signal (8 mA) was generated by a proprietary device designed by ReShape Lifesciences Inc. (San Clemente, CA). One hour following the all procedures (except for 15 min following the HFAC+Stimulation procedure) a blood sample was taken from a cut end of the rat's tail. An AlphaTrak (Abbott Laboratories, North Chicago, IL, USA) blood glucose monitor was used to measure blood glucose concentrations (mg/dL).

Next, an IVGTT was performed. The IVGTT consisted of an IV injection into the port of a 0.5 g/kg dose of glucose made up in 0.9% saline with a 20% weight/volume concentration. Blood glucose was then sampled for 30 min following the glucose injection. Stimulation and/or delivery of HFAC were maintained during the IVGTT. In some cases a subsequent IVGTT was administered in the Sham group and following the cessation of HFAC and stimulation in the HFAC+Stimulation group. All data are presented as mean±SEM. Percent change in glucose concentration was calculated using the following equation:

% Change=((Blood glucose concentration at time $x$–Baseline blood glucose concentration)/(Baseline blood glucose concentration))*100

Results

Electrical modulation of nerves innervating the pancreas and liver improved performance on an IVGTT in the Zucker obese (fatty) rat (ZDF fa/fa) model of T2DM. The celiac branch of the vagus nerve was stimulated (1 Hz) with either simultaneous ligation of the hepatic branch of the vagus nerve or application of HFAC (5000 Hz) to the hepatic nerve. The description herein indicates that celiac stimulation causes an increase in plasma insulin however plasma glucose is either unchanged or increased. Without being bound, it is believed that this is due to simultaneous pancreatic release of glucagon; causing hepatic glucose release. By blocking conduction through the hepatic branch it is hypothesized that attenuation of liver sensitivity to glucagon is achieved. Also, it has been shown that hepatic vagotomy decreases insulin resistance in a rodent model of Type 2 diabetes.

Figure 9:
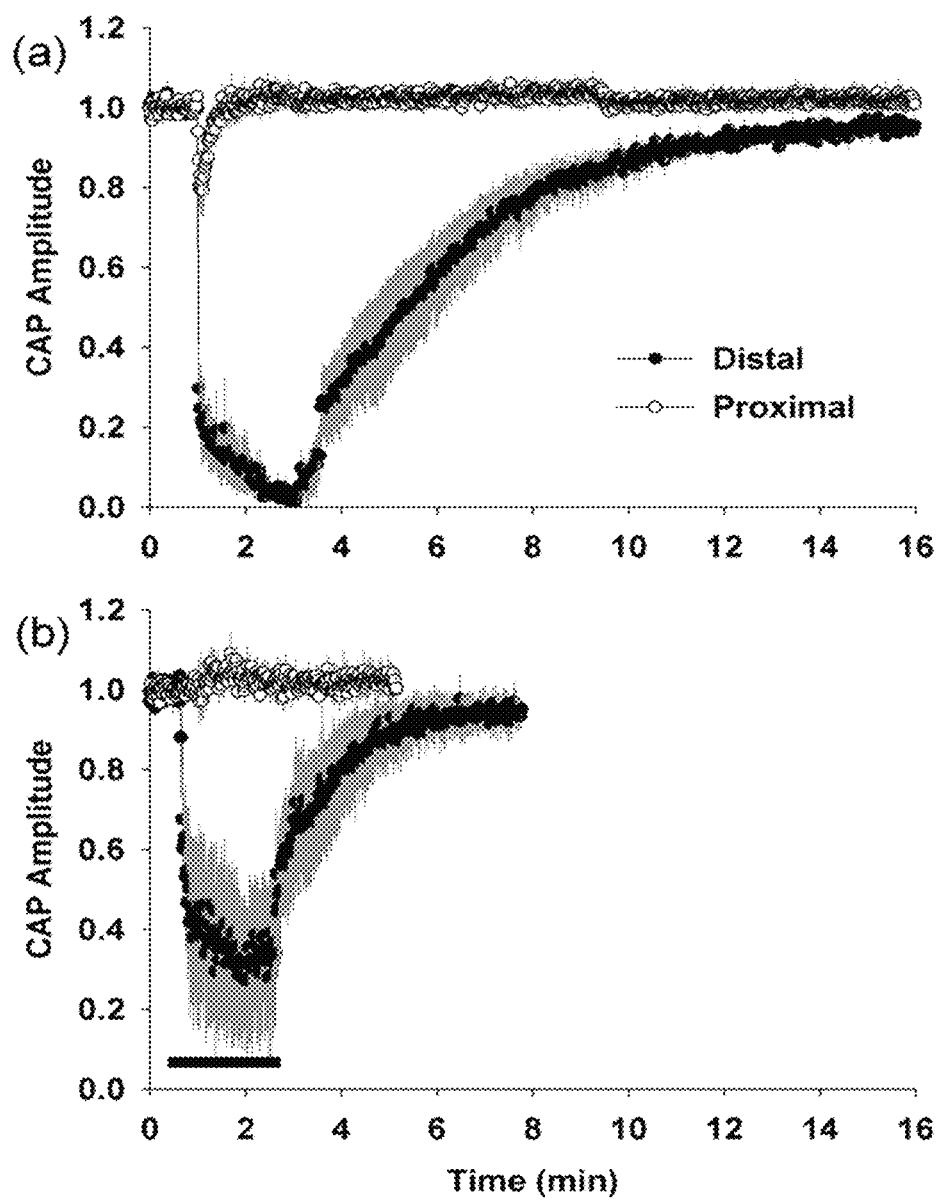
FIG. 9 is a graphical illustration of HFAC induced conduction block of the vagus nerve occurred at the site of the blocking electrode for the C waves.

FIG. 9 is a graphical illustration of HFAC induced conduction block of the vagus nerve occurred at the site of the blocking electrode for the C waves. As shown, the CAP generated by the proximal (control) electrode was not considerably depressed compared to the CAP elicited by the distal electrode during the following HFAC at a duration of 120 sec. at 10 mA (10a) and 8 mA (10b). The data indicated that the attenuation of the distal CAP was primarily due to conduction block at the site of the blocking electrode. As shown in FIG. 9, the solid line indicates application of HFAC.

Figure 10:
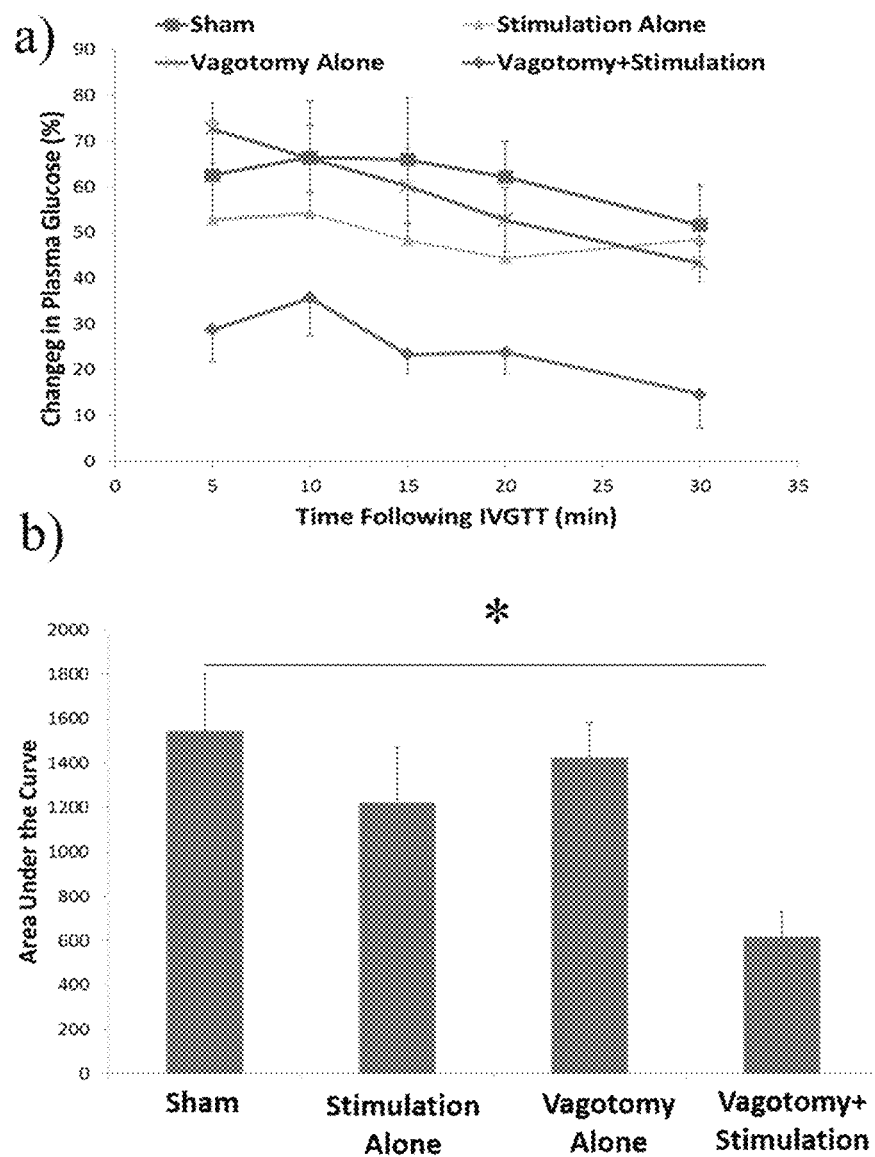
FIG. 10 depicts hepatic vagotomy in combination with celiac stimulation improved performance on an IVGTT. 10a is a graphical representation of changes in PG following an IVGTT. 10b is a graphical representation of Area under the curve analyses following the injection of glucose.

FIG. 10 depicts hepatic vagotomy in combination with celiac stimulation improved performance on an IVGTT. FIG. 10a is a graphical representation of changes in PG following an IVGTT. 10b is a graphical representation of Area under the Curve analyses following the injection of glucose. FIG. FIG. 10a represents changes in PG following IVGTT with a sham operation, celiac stimulation alone, hepatic vagotomy alone and the combination of stimulation of the celiac branch with a hepatic vagotomy are shown. Referring to FIG. 10b the Area under the Curve analyses following the injection of glucose had a p value of 0.007. Further, the subjects had a fasting plasma glucose level of 287±mg/dL.

Figure 11:
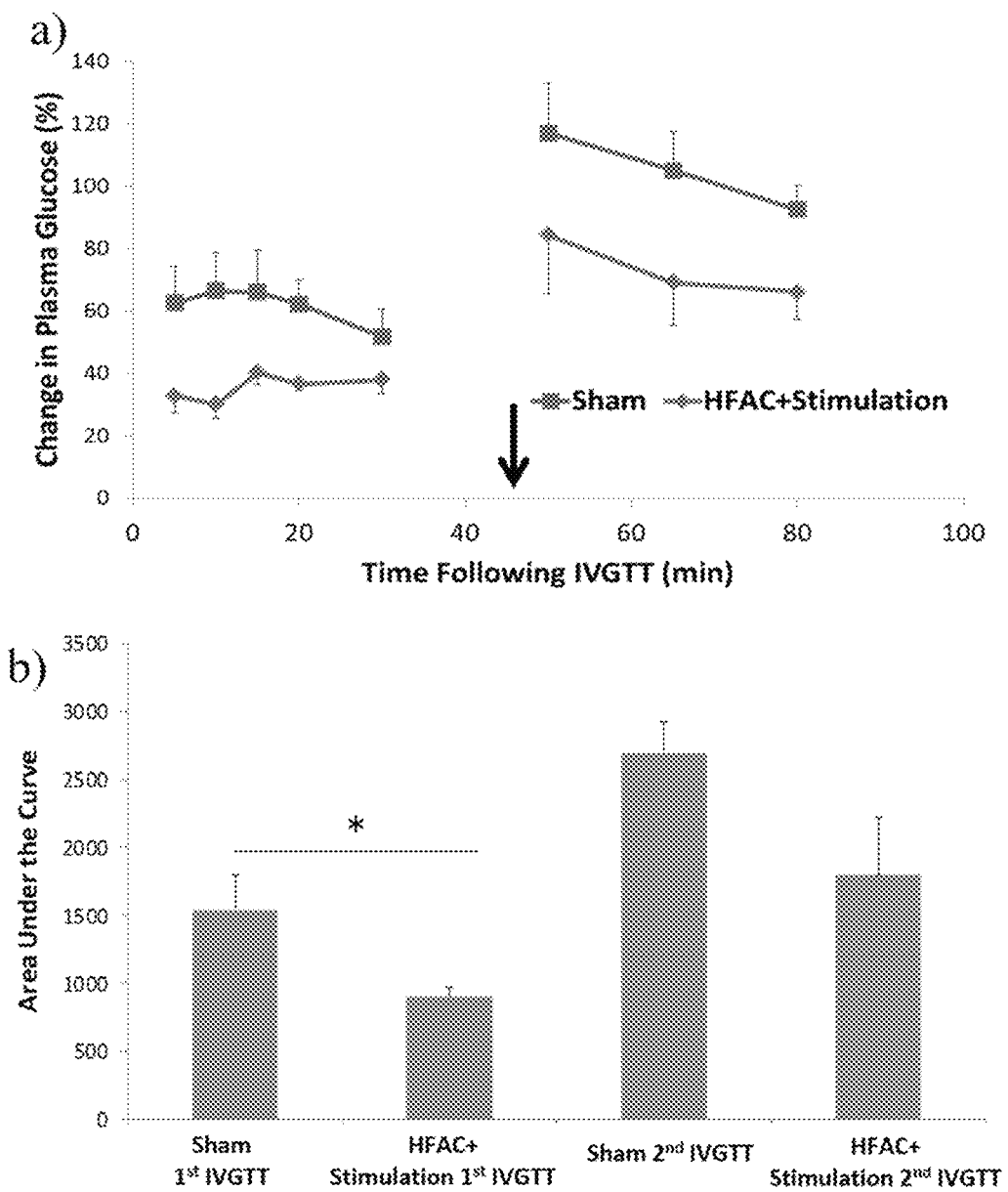
FIG. 11 shows simultaneous stimulation of the celiac branch and the block of the hepatic Branch reversibly improved person on an IVGTT; 11a is a graphical representation of changes in PG following an IVGTT; 11b is a graphical representation of Area under the Curve analyses following two injections of glucose.

FIG. 11 shows simultaneous stimulation of the celiac branch and the Block of the Hepatic Branch reversibly improved performance on an IVGTT. FIG. 11a is a graphical representation of changes in PG following an IVGTT. Changes in PG following an IVGTT for a sham or stimulation+vagotomy. In this case a subsequent IVGTT was performed (arrow) 15 minutes following the cessation of the HFAC stimulation. FIG. 11b is a graphical representation of Area under the Curve analyses following two injections of glucose. The p-value was determined to be 0.027.

Figure 12:
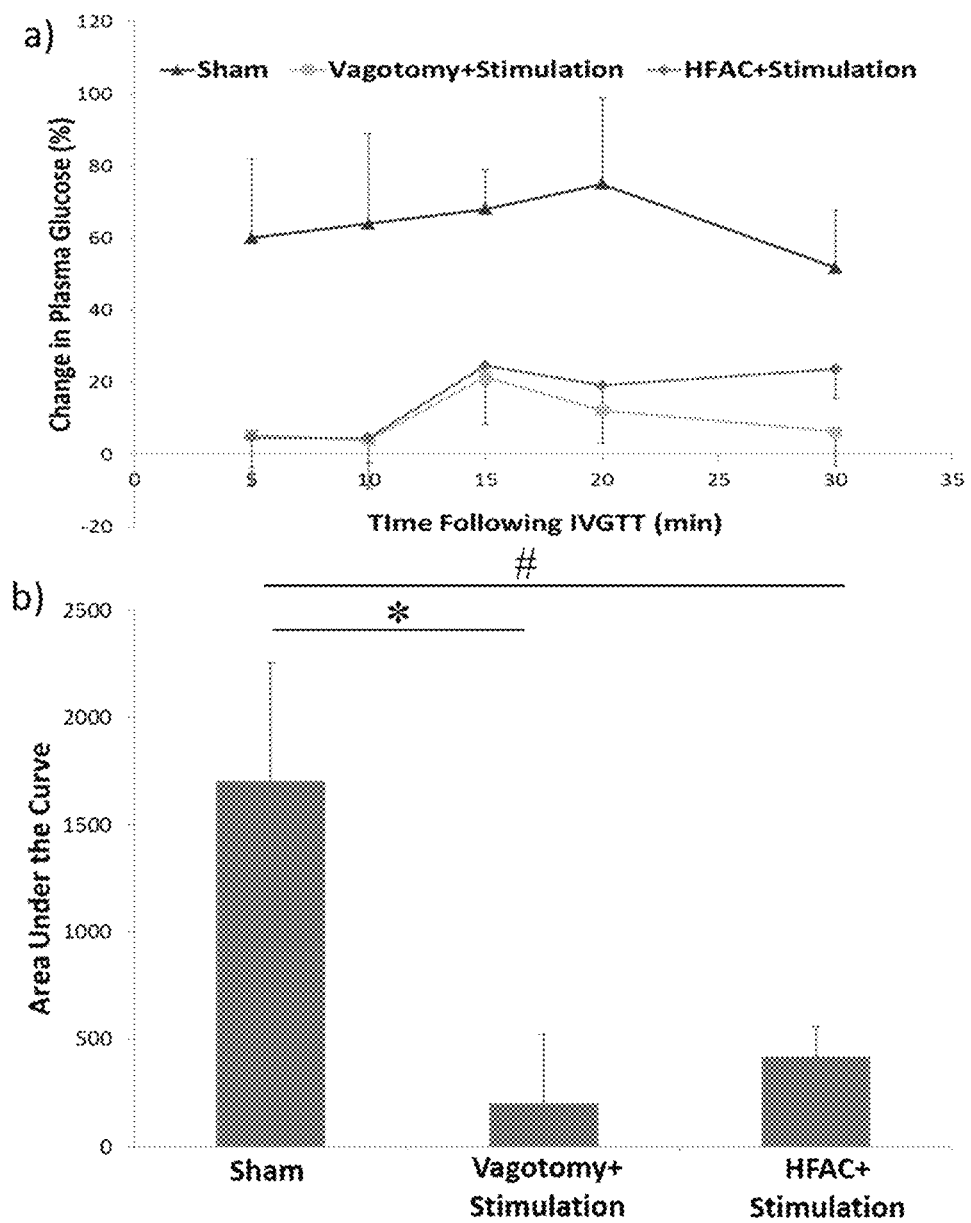
FIG. 12 shows simultaneous stimulation of the Celiac Branch and the HFAC block of the hepatic branch improved performance on an IVGTT in a non-diabetic rat control; 12a represents the change in PG following sham; 12b is a graphical representation of Area under the Curve analyses following the injection of glucose.

FIG. 12 shows simultaneous stimulation of the Celiac Branch and the HFAC block of the hepatic branch improved performance on an IVGTT in a non-diabetic rat control. FIG. 12a represents the change in PG following sham. Change in PG following a sham, vagotomy+stimulation and HFAC+ stimulation are shown. FIG. 12b is a graphical representation of Area under the Curve analyses following the injection of glucose for various procedures. Non-diabetic controls has a fasting plasma glucose level of 167±14 mg/dL.

The data in FIGS. 10-12 indicates that electrical modulation of nerves innervating the pancreas and liver improved performance on an IVGTT when the method of stimulating the celiac branch of the vagus nerve (innervating the pancreas) at 1 Hz in combination with either simultaneous ligation of the hepatic branch of the vagus nerve or application of HFAC (5000 Hz) to the hepatic nerve. While not wanting to be bound by a particular theory, this is likely due to simultaneous pancreatic release of glucagon; causing hepatic glucose release. By blocking conduction through the hepatic branch this attenuates the livers sensitivity to glucagon.

Figure 13:
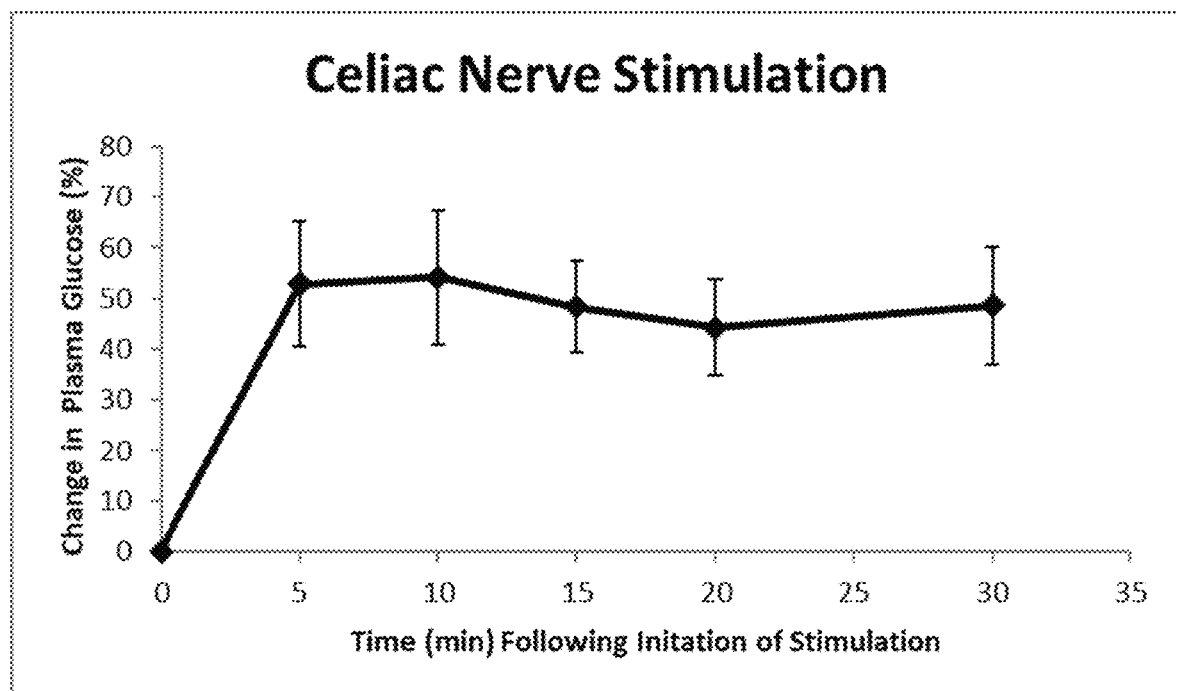
FIG. 13 shows stimulation parameters for an example celiac nerve stimulation.
Figure 14:
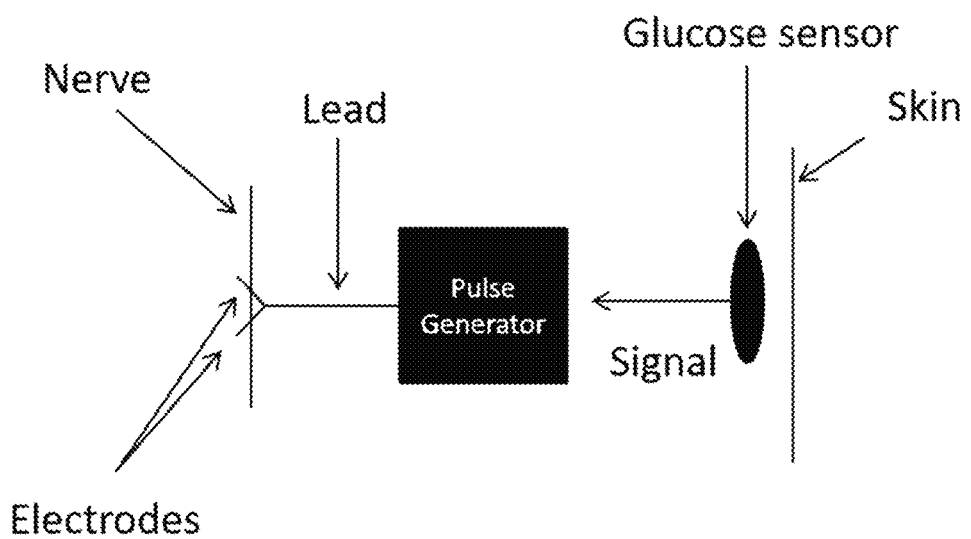
FIG. 14 shows a schematic of system in which an implantable glucose sensor communicates with a pulse generator to initiate vagus nerve stimulation.
Figure 15:
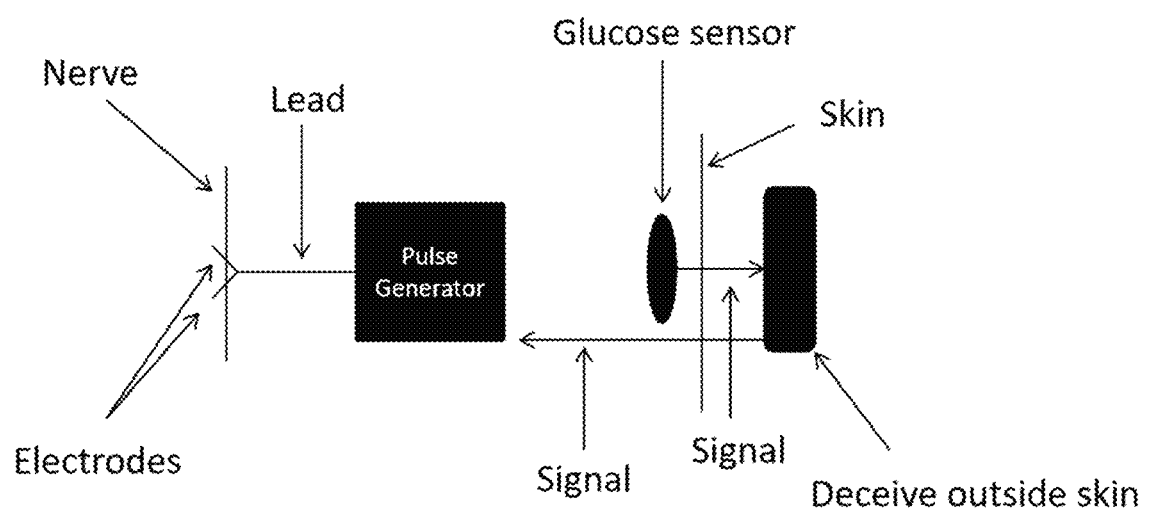
FIG. 15 shows a schematic of system in which an implantable glucose sensor communicates first with an external device attached to the outside of the skin which then communicates with the pulse generator to initiate vagus nerve stimulation.

Referring now to FIGS. 13-15, where neuromodulation for the treatment of the hypoglycemic state is described. The system described herein offers a treatment for hypoglycemia in type 1 diabetics. The average individual with type 1 diabetes experiences about two episodes of symptomatic hypoglycemia per week. Severe hypoglycemia has an annual prevalence of 30-40% and an annual incidence of 1.0-1.7 episodes per patient per year.

It should be noted that hypoglycemia is not only observed in diabetics but also arises from other diseases such as, but not limited to, kidney failure, certain tumors, liver disease, hypothyroidism, inborn errors of metabolism, severe infections, reactive hypoglycemia, and a number of drugs including alcohol use. The proposed device may help treat hypoglycemia in patents with these medical conditions.

FIG. 13 shows stimulation parameters were continuous 1 Hz, 4 ms pulse width 8 mA current amplitude. This data demonstrates that stimulation alone of the vagus nerve celiac branch, or posterior vagal trunk above the branching point of the celiac, causes a quick (5 min or less) and significant increase in PG (FIG. 13). It is important to note that, continuous stimulation would not be ideal due to complications of hyperglycemia. A system that monitors PG levels and then initiates, or adjusts, vagus nerve stimulation when PG decreases to an unsafe level would be desirable.

Referring to FIGS. 14-15, wherein the system would include a pulse generator, leads that are placed on the vagus nerve and an implantable glucose sensor (to monitor blood glucose levels). The sensor sampling rate would be from about 1 second to 10 min. FIG. 14 shows a schematic of system in which an implantable glucose sensor communicates with a pulse generator to initiate vagus nerve stimulation. The implantable sensor would detect low blood glucose levels and send a signal to turn the pulse generator on. FIG. 15 shows a schematic of system in which an implantable glucose sensor communicates first with an external device attached to the outside of the skin which then communicates with the pulse generator to initiate vagus nerve stimulation.

The communication between the pulse generator and the glucose sensor can be through, but not limited to, blue tooth technology, radio frequency, WIFI, light or sound. In some embodiments the glucose sensor would be below the layer of the skin and communicate to a device outside of the skin with a battery to power wireless communication. The communication between the glucose sensor and the device outside the body can be through, but not limited to, blue tooth technology, radio frequency, WIFI, light or sound. The device outside of the skin would then communicate with the pulse generator through, but not limited to, blue tooth technology, radio frequency, WIFI, light or sound. The implantable glucose sensor, or the external device that communicates with the implantable glucose sensor, could also communicate with a smart device (such as a phone running an app) to display blood glucose levels and send an alarm when blood glucose reaches an unsafe low level. The communication to the smart device can be through, but not limited to, blue tooth technology, radio frequency, WIFI, light or sound. Stimulation parameters include a frequency range between 0.01 Hz to 200 Hz, current or voltage amplitude range: 0.1 mA to 12 mA or 0.1 to 12 volts, pulse width range: 0.1 ms to 10 ms. Stimulation can be continuous or bursting with inter-burst intervals ranging from milliseconds, seconds to minuets.

Site of stimulation include any segment of the vagus nerve. This includes sub-diaphragmatic anterior or posterior vagal trunks and branches of the sub-diaphragmatic vagal trunks such as the celiac branch originating from the posterior vagal trunk, the accessory celiac branch, originating from the anterior vagal trunk or the hepatic branch, originating from the anterior vagal trunk. Sites of stimulation also include the anterior or posterior thoracic vagus, or the left or right cervical vagus. Any combination of vagus nerve stimulation sites is included.

Modifications and equivalents of disclosed concepts such as those which might readily occur to one skilled in the art are intended to be included in the scope of the claims which are appended hereto. In addition, this disclosure contemplates application of a combination of electrical signal treatment by placement of electrodes on one or more nerves. Any publications referred to herein are hereby incorporated by reference.

What is claimed is:

1. A system for treating a patient with impaired glucose regulation, the system comprising:
   at least two electrodes, wherein the at least two electrodes include a first electrode and a second electrode,
      wherein the first electrode is operably connected to a first distal end of a first lead assembly, wherein an implantable pulse generator is operably connected to a second distal end of the first lead assembly,
   wherein the second electrode is operably connected to a first distal end of a second lead assembly, wherein the implantable pulse generator is operably connected to a second distal end of the second lead assembly, wherein at least one of the at least two electrodes is adapted to be placed on a first target nerve or organ;
   the implantable pulse generator comprising a power module and a programmable therapy delivery module, wherein the programmable therapy delivery module is configured to deliver a first therapy program comprising a first electrical signal treatment applied to the first target nerve or organ, wherein the first electrical signal has a frequency selected to initiate activity on the first target nerve or organ;
   an external component comprising a communication system and a programmable storage and communication module, wherein programmable storage and communication module is configured to store the first therapy program and to communicate the first therapy program to the implantable pulse generator and wherein the activity is an electrical stimulation or an electrical block; and a glucose monitor capable of communicating with the system for treating a patient with impaired glucose regulation, wherein the programmable therapy delivery module is configured to deliver a second therapy program comprising a second electrical signal treatment applied to a second target nerve or organ, and wherein the second electrical signal has a frequency selected to upregulate or down-regulate activity on the second target nerve or organ, wherein the frequency is selected to either up-regulate or down-regulate activity on the second target nerve or organ based on opposing the activity initiated on the first target nerve or organ.

2. The system of claim 1, wherein the at least one electrode is adapted to be placed on a first organ selected from the spleen, stomach, duodenum, pancreas, liver and ileum.

3. The system of claim 1, wherein the at least one electrode is adapted to be placed at a first nerve selected from a vagus nerve, a splanchnic nerve, a hepatic branch of the vagus nerve, a celiac branch of the vagus nerve, and combinations thereof.

4. The system of claim 1, wherein the programmable therapy delivery module is configured to deliver the first electrical signal having a frequency of at least 200 Hz.

5. The system of claim 1, wherein the programmable storage and communication module is configured to deliver the first therapy program to the implantable pulse generator, wherein the first therapy program comprises an electrical signal treatment applied intermittently multiple times in a day and over multiple days, wherein the electrical signal has a frequency selected to downregulate activity on the first target nerve or organ and has an on time and an off time, wherein the off time is selected to allow at least a partial recovery of the activity of the target nerve or organ.

6. The system of claim 1, further comprising a sensor operably connected to the implantable pulse generator, wherein the sensor detects an increase or decrease of blood glucose from a threshold level.

7. The system of claim 1, wherein the first or second signal has a frequency between 0.01 Hz and less than 200 Hz.

8. A method of improving glycemic control of a subject, the method comprising:
applying the first electrical signal to the first target nerve or organ of the subject having impaired glucose regulation using the system of claim 1, wherein the first electrical signal initiates a neural stimulation or a neural block, wherein the first electrical signal is applied followed by an off time during which the first electrical signal is not applied to the nerve, wherein the off time is initiated when blood glucose levels are detected between 80 mg/dL and 110 mg/dL, wherein the first electrical signal is applied multiple times per day to alter the blood glucose levels.

9. The method of claim 8, wherein the first electrical signal is off time is applied when blood glucose levels are detected between 80 mg/dL and 110 mg/dL, and wherein the glucose monitor initiates the on time signal frequency, wherein the on time frequency adjusts signal up or adjust signal down when blood glucose levels are below 80 mg/dL or above 110 mg/dL and wherein the frequency initiated can be the same, lower or greater than the previous on time signal.

10. The method of claim 8, further comprising applying the second electrical signal to the second target nerve or organ.

11. The method of claim 10, wherein the first electrical signal down-regulates the activity initiated on the first target nerve or organ and the second electrical signal up-regulates the activity initiated on the second target nerve or organ, and wherein the down-regulating and up-regulating signals are applied at the same time or at different times.

12. The method of claim 10, wherein the second target nerve or organ is a splanchnic nerve, a celiac branch of a vagus nerve, or a pancreas.

13. The method of claim 8, further comprising administering an agent that improves glucose control, wherein the agent increases an amount of insulin and/or increases a sensitivity of cells to insulin.

14. A method of making a system for treating a patient with impaired glucose regulation comprising:
connecting a first electrode to a first distal end of a first lead assembly;
connecting a second distal end of the first lead assembly to an implantable pulse generator;
connecting a second electrode to a first distal end of a second lead assembly;
connecting a second distal end of the second distal assembly to the implantable pulse generator,
wherein the first electrode is adapted to be placed on a first target nerve or organ;
configuring a programmable therapy delivery module of the implantable pulse generator to deliver a first therapy program comprising a first electrical signal treatment applied to the first target nerve or organ; and
configuring a programmable storage and communication module of an external component to store the first therapy program and to communicate the first therapy program to the implantable pulse generator; and configuring a glucose monitor to communicate with the system for treating a patient with impaired glucose regulation,
wherein the programmable therapy delivery module is configured to deliver a second therapy program comprising a second electrical signal treatment applied to a second target nerve or organ, and
wherein the second electrical signal has a frequency selected to upregulate or down-regulate activity on the second target nerve or organ, wherein the frequency is selected to either up-regulate or down-regulate activity on the second target nerve or organ based on opposing the activity initiated on the first target nerve or organ.

15. The method of claim 14, further comprising connecting a sensor to the implantable pulse generator.

16. The method of claim 15, further comprising configuring the programmable therapy delivery module of the implantable pulse generator to deliver the second therapy program upon a signal from the sensor.

17. The method of claim 14, wherein the first electrode is adapted to be placed on a hepatic branch of a vagus nerve and the second electrode is adapted to be placed on the vagus nerve at a location selected from among: a celiac branch of the vagus nerve, a dorsal vagus nerve above a branching point of the celiac nerve, or a ventral vagus nerve above a branching point of the hepatic nerve.

18. The method of claim 14, wherein the electrical signal has a frequency selected to downregulate activity on the first target nerve or organ and has an off time, wherein the off time is selected to allow at least a partial recovery of the activity of the first target nerve or organ.

19. The system of claim 6, wherein upon detecting a change in blood glucose from a predetermined threshold level the sensor will communicate to the pulse generator to turn on or alter the frequency, a pulse width, or an amplitude of the first or second electrical signal to treat hyperglycemia or hypoglycemia.

20. A method of improving glycemic control of a subject, the method comprising:

- placing, on a first target nerve or organ, a first electrode of a plurality of electrodes, wherein each of the plurality of electrodes are individually operably connected to an implantable pulse generator by one of a plurality of lead assemblies, each one of the plurality of lead assemblies connecting at a first distal end to one of the plurality of electrodes and at a second distal end to the implantable pulse generator; and a glucose monitor capable of communicating with the system for treating a patient with impaired glucose regulation,
  - wherein the plurality of electrodes comprises at least two electrodes,
  - wherein the first electrode of a plurality of electrodes is adapted to be placed on the first target nerve or organ,
  - wherein the implantable pulse generator comprises a power module and a programmable therapy delivery module,
  - wherein the programmable therapy delivery module is configured to deliver at least one therapy program comprising a first electrical signal treatment applied to the first target nerve or organ,
  - wherein the first electrical signal has a frequency selected to initiate activity on the first target nerve or organ, wherein the activity comprises a neural stimulation or a neural block;
- receiving, at the implantable pulse generator, the at least one therapy program via a communication system of an external component, wherein the external component comprises the communication system and a programmable storage and communication module, wherein the programmable storage and communication module is configured to store the at least one therapy program;
- applying the first electrical signal treatment to the first target nerve or organ of the subject having impaired glucose regulation, wherein the first electrical signal treatment is applied continuously followed by an off time of a plurality of off times during which the first electrical signal is not applied to the first target nerve or organ, wherein the plurality of off times are applied multiple times per day when blood glucose levels are detected by the glucose monitor to be between 80 mg/dL and 110 mg/dL; and
- applying a second electrical signal treatment to a second target nerve or organ of the subject having impaired glucose regulation, wherein the second electrical signal treatment has a frequency selected to upregulate or down-regulate activity on the second target nerve or organ, wherein the frequency is selected to either upregulate or down-regulate activity on the second target nerve or organ based on opposing the activity initiated on the first target nerve or organ.

* * * * *